(12) United States Patent
Yang

(10) Patent No.: US 8,586,830 B2
(45) Date of Patent: Nov. 19, 2013

(54) IOSLATED TT1 POLYNUCLEOTIDE, ENCODED PROTEINS AND VECTORS FOR INCREASING TOLERANCE OF PLANTS AND MICROBES TO ABIOTIC STRESSES AND THE USE THEREOF

(75) Inventor: Yi Yang, Sichuan (CN)

(73) Assignee: Sichuan Biodesign Gene Engineering Co., Ltd., Chengdu (CN)

( * ) Notice: Subject to any disclaimer, the term of this patent is extended or adjusted under 35 U.S.C. 154(b) by 232 days.

(21) Appl. No.: 13/055,299

(22) PCT Filed: Jul. 23, 2009

(86) PCT No.: PCT/CN2009/072888
§ 371 (c)(1),
(2), (4) Date: Jan. 21, 2011

(87) PCT Pub. No.: WO2010/020143
PCT Pub. Date: Feb. 25, 2010

(65) Prior Publication Data
US 2011/0258740 A1 Oct. 20, 2011

(30) Foreign Application Priority Data
Jul. 29, 2008 (CN) .......................... 2008 1 0045667

(51) Int. Cl.
*C07K 14/415* (2006.01)
*C12N 1/00* (2006.01)
*C12N 15/09* (2006.01)
*C12N 15/63* (2006.01)
*C12N 15/67* (2006.01)
*C12N 15/82* (2006.01)
*C07H 21/00* (2006.01)
*A01H 3/00* (2006.01)
*A01H 5/00* (2006.01)
*C07H 21/04* (2006.01)

(52) U.S. Cl.
USPC ......... 800/289; 536/23.6; 536/23.1; 435/410; 435/243; 435/320.1; 435/419; 800/278; 800/295; 800/298

(58) Field of Classification Search
None
See application file for complete search history.

(56) References Cited

U.S. PATENT DOCUMENTS 7,834,146 B2 * 11/2010 Kovalic et al. ................ 530/350
2011/0321197 A1 * 12/2011 Schon et al. .................. 800/290

FOREIGN PATENT DOCUMENTS

WO    WO2008034648    *  3/2008    ............. C12N 15/82

OTHER PUBLICATIONS

Applehagen et al. Transparent TESTA1 interacts with R2R3-MYB factors and affects early and late steps of flavonoid biosynthesis in the endothelium of *Arabidopsis thaliana* seeds. The Plant Journal. 2011. 67: 406-419.*

* cited by examiner

*Primary Examiner* — Cathy Kingdon Worley
*Assistant Examiner* — Ashley K Buran
(74) *Attorney, Agent, or Firm* — Caesar, Rivise, Bernstein, Cohen & Pokotilow, Ltd.

(57) ABSTRACT

The TT1 gene, the recombinant expression vector containing the gene, the polypeptide encoded by the gene and the use thereof are provided. The TT1 gene can effectively increase tolerance of plants and microbes to abiotic stresses, such as drought, acid-alkaline, saline-alkaline and heat. The methods for producing transgenic plants and microbes are also provided. The methods are simple and effective. The transgenic plants and microbes exhibit enhanced tolerance to environmental stresses.

14 Claims, 6 Drawing Sheets

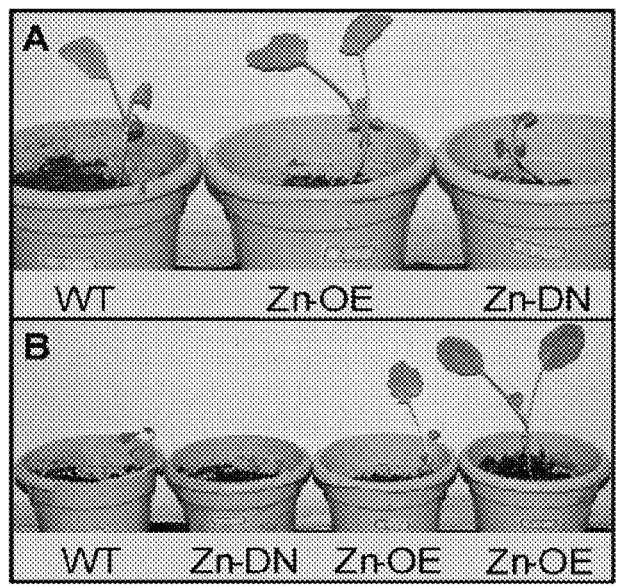
Fig. 5
| Lines | Zn-OE | Zn-DN | WT |
|---|---|---|---|
| Zn/Actin | 2.5x | 0.5x | 1x |
| TT1 | | | |
| Actin | | | |
Fig. 6
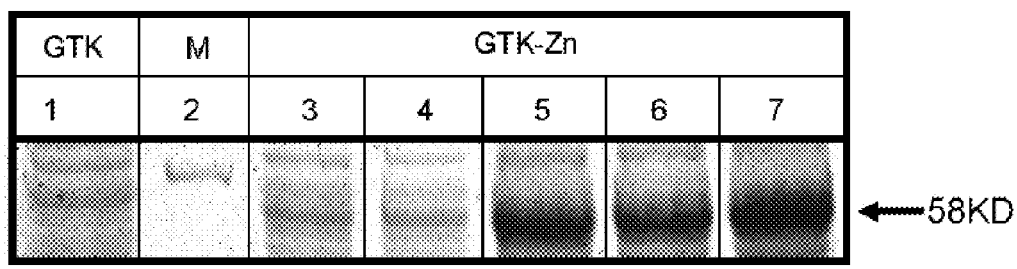
Fig. 7

SEQUENCE LISTING

<160> NUMBER OF SEQ ID NOS: 24

<210> SEQ ID NO 1
<211> LENGTH: 861
<212> TYPE: DNA
<213> ORGANISM: Brassica napus
<220> FEATURE:

<221> NAME/KEY: CDS
<222> LOCATION: (1)..(861)
<223> OTHER INFORMATION: cDNA sequence of genes which increase tolerance of plants and microbes to abiotic stresses

<400> SEQUENCE: 1

```
atg tcg gat gat ttg agt tta tgt acc gat cgt ctg ata acg gcc gag      48
Met Ser Asp Asp Leu Ser Leu Cys Thr Asp Arg Leu Ile Thr Ala Glu
1               5                   10                  15 agc ttg gaa tca gaa aag gat tct gga gaa agt tcc agg ctt caa ggc      96
Ser Leu Glu Ser Glu Lys Asp Ser Gly Glu Ser Ser Arg Leu Gln Gly
            20                  25                  30 aaa gat gtg gct tct tct tca tct gcg gat gaa gct gaa gat gct agg     144
Lys Asp Val Ala Ser Ser Ser Ser Ala Asp Glu Ala Glu Asp Ala Arg
        35                  40                  45 aag tac tat gct gtt gtt gca gaa gag gag ccg ctt ctg caa tct gtt     192
Lys Tyr Tyr Ala Val Val Ala Glu Glu Glu Pro Leu Leu Gln Ser Val
    50                  55                  60 gag tgc cgt att tgc cag gag gaa gat atc act aag aac ttg gag act     240
Glu Cys Arg Ile Cys Gln Glu Glu Asp Ile Thr Lys Asn Leu Glu Thr
65                  70                  75                  80 cct tgt gct tgc aat ggc agt ttg aag tat gct cac cgc aag tgt gtt     288
Pro Cys Ala Cys Asn Gly Ser Leu Lys Tyr Ala His Arg Lys Cys Val
                85                  90                  95 cag cgt tgg tgt aat gag aaa ggc gac ata atc tgc gaa ata tgc cac     336
Gln Arg Trp Cys Asn Glu Lys Gly Asp Ile Ile Cys Glu Ile Cys His
            100                 105                 110 cag cct tat caa tct gga tat aca gca cct cca cct cct cct cct gat     384
Gln Pro Tyr Gln Ser Gly Tyr Thr Ala Pro Pro Pro Pro Pro Pro Asp
        115                 120                 125 gaa act ata att cac att ggt gac gac tgg gag gat gga gtt cac ttg     432
Glu Thr Ile Ile His Ile Gly Asp Asp Trp Glu Asp Gly Val His Leu
    130                 135                 140 gac tcg agc gac ccg cgc att cta gca atg gct gcg gcg gaa cga cat     480
Asp Ser Ser Asp Pro Arg Ile Leu Ala Met Ala Ala Ala Glu Arg His
145                 150                 155                 160 ttc ttg gaa gct gac tat gac gag tac tct gag tct aac tct agc ggt     528
Phe Leu Glu Ala Asp Tyr Asp Glu Tyr Ser Glu Ser Asn Ser Ser Gly
                165                 170                 175 gct gcc ttc tgt cgc tct gct gct ctc atc ctg atg gca ctt tta ctg     576
Ala Ala Phe Cys Arg Ser Ala Ala Leu Ile Leu Met Ala Leu Leu Leu
            180                 185                 190 tta cgt gat gca cta aac ctc aca act aac cca gat gac gag gac gat     624
Leu Arg Asp Ala Leu Asn Leu Thr Thr Asn Pro Asp Asp Glu Asp Asp
        195                 200                 205 ccc act gcc ttc ttc tct ctt ttc ctt ctt cgt gct gct ggt ttt ctc     672
Pro Thr Ala Phe Phe Ser Leu Phe Leu Leu Arg Ala Ala Gly Phe Leu
    210                 215                 220 ctc cca tgt tat atc atg gca tgg gcc atc ggt att ctc cag cgc cgg     720
Leu Pro Cys Tyr Ile Met Ala Trp Ala Ile Gly Ile Leu Gln Arg Arg
225                 230                 235                 240 agg caa aga cag gaa gca gct gcg cta gct gcg gcg gaa gtt gcc ttc     768
Arg Gln Arg Gln Glu Ala Ala Ala Leu Ala Ala Ala Glu Val Ala Phe
                245                 250                 255 atg ata cac ggt ggt gtg cca caa cgc agg gga cta cac ttt gct gta     816
Met Ile His Gly Gly Val Pro Gln Arg Arg Gly Leu His Phe Ala Val
            260                 265                 270 gca cca gag cag ccg ccg cca ata tcc aac cca aca cca gtc tga         861
Ala Pro Glu Gln Pro Pro Pro Ile Ser Asn Pro Thr Pro Val
        275                 280                 285
```

<210> SEQ ID NO 2
<211> LENGTH: 286
<212> TYPE: PRT
<213> ORGANISM: Brassica napus

<400> SEQUENCE: 2

Met Ser Asp Asp Leu Ser Leu Cys Thr Asp Arg Leu Ile Thr Ala Glu
1               5                   10                  15

Ser Leu Glu Ser Glu Lys Asp Ser Gly Glu Ser Arg Leu Gln Gly
            20                  25                  30

Lys Asp Val Ala Ser Ser Ser Ala Asp Glu Ala Glu Asp Ala Arg
        35                  40                  45

Lys Tyr Tyr Ala Val Val Ala Glu Glu Pro Leu Leu Gln Ser Val
    50                  55                  60

Glu Cys Arg Ile Cys Gln Glu Glu Asp Ile Thr Lys Asn Leu Glu Thr
65                  70                  75                  80

Pro Cys Ala Cys Asn Gly Ser Leu Lys Tyr Ala His Arg Lys Cys Val
                85                  90                  95

Gln Arg Trp Cys Asn Glu Lys Gly Asp Ile Ile Cys Glu Ile Cys His
            100                 105                 110

Gln Pro Tyr Gln Ser Gly Tyr Thr Ala Pro Pro Pro Pro Pro Asp
        115                 120                 125

Glu Thr Ile Ile His Ile Gly Asp Asp Trp Glu Asp Gly Val His Leu
130                 135                 140

Asp Ser Ser Asp Pro Arg Ile Leu Ala Met Ala Ala Ala Glu Arg His
145                 150                 155                 160

Phe Leu Glu Ala Asp Tyr Asp Glu Tyr Ser Glu Ser Asn Ser Ser Gly
                165                 170                 175

Ala Ala Phe Cys Arg Ser Ala Ala Leu Ile Leu Met Ala Leu Leu Leu
            180                 185                 190

Leu Arg Asp Ala Leu Asn Leu Thr Thr Asn Pro Asp Asp Glu Asp Asp
        195                 200                 205

Pro Thr Ala Phe Phe Ser Leu Phe Leu Leu Arg Ala Ala Gly Phe Leu
    210                 215                 220

Leu Pro Cys Tyr Ile Met Ala Trp Ala Ile Gly Ile Leu Gln Arg Arg
225                 230                 235                 240

Arg Gln Arg Gln Glu Ala Ala Ala Leu Ala Ala Ala Glu Val Ala Phe
                245                 250                 255

Met Ile His Gly Gly Val Pro Gln Arg Arg Gly Leu His Phe Ala Val
            260                 265                 270

Ala Pro Glu Gln Pro Pro Pro Ile Ser Asn Pro Thr Pro Val
        275                 280                 285

<210> SEQ ID NO 3
<211> LENGTH: 696
<212> TYPE: DNA
<213> ORGANISM: Brassica napus
<220> FEATURE:
<221> NAME/KEY: CDS
<222> LOCATION: (1)..(696)
<223> OTHER INFORMATION: nucleotide sequence of proteins which interact
      with ATP6

<400> SEQUENCE: 3 gaa gag gag ccg ctt ctg caa tct gtt gag tgc cgt att tgc cag gag    48
Glu Glu Glu Pro Leu Leu Gln Ser Val Glu Cys Arg Ile Cys Gln Glu
1               5                   10                  15 gaa gat atc act aag aac ttg gag act cct tgt gct tgc aat ggc agt    96
Glu Asp Ile Thr Lys Asn Leu Glu Thr Pro Cys Ala Cys Asn Gly Ser

```
                        20                  25                  30
ttg aag tat gct cac cgc aag tgt gtt cag cgt tgg tgt aat gag aaa        144
Leu Lys Tyr Ala His Arg Lys Cys Val Gln Arg Trp Cys Asn Glu Lys
         35                  40                  45 ggc gac ata atc tgc gaa ata tgc cac cag cct tat caa tct gga tat        192
Gly Asp Ile Ile Cys Glu Ile Cys His Gln Pro Tyr Gln Ser Gly Tyr
 50                  55                  60 aca gca cct cca cct cct cct cct gat gaa act ata att cac att ggt        240
Thr Ala Pro Pro Pro Pro Pro Pro Asp Glu Thr Ile Ile His Ile Gly
 65                  70                  75                  80 gac gac tgg gag gat gga gtt cac ttg gac tcg agc gac ccg cgc att        288
Asp Asp Trp Glu Asp Gly Val His Leu Asp Ser Ser Asp Pro Arg Ile
                 85                  90                  95 cta gca atg gct gcg gcg gaa cga cat ttc ttg gaa gct gac tat gac        336
Leu Ala Met Ala Ala Ala Glu Arg His Phe Leu Glu Ala Asp Tyr Asp
            100                 105                 110 gag tac tct gag tct aac tct agc ggt gct gcc ttc tgt cgc tct gct        384
Glu Tyr Ser Glu Ser Asn Ser Ser Gly Ala Ala Phe Cys Arg Ser Ala
        115                 120                 125 gct ctc atc ctg atg gca ctt tta ctg tta cgt gat gca cta aac ctc        432
Ala Leu Ile Leu Met Ala Leu Leu Leu Leu Arg Asp Ala Leu Asn Leu
    130                 135                 140 aca act aac cca gat gac gag gac gat ccc act gcc ttc ttc tct ctt        480
Thr Thr Asn Pro Asp Asp Glu Asp Asp Pro Thr Ala Phe Phe Ser Leu
145                 150                 155                 160 ttc ctt ctt cgt gct gct ggt ttt ctc ctc cca tgt tat atc atg gca        528
Phe Leu Leu Arg Ala Ala Gly Phe Leu Leu Pro Cys Tyr Ile Met Ala
                165                 170                 175 tgg gcc atc ggt att ctc cag cgc cgg agg caa aga cag gaa gca gct        576
Trp Ala Ile Gly Ile Leu Gln Arg Arg Arg Gln Arg Gln Glu Ala Ala
            180                 185                 190 gcg cta gct gcg gcg gaa gtt gcc ttc atg ata cac ggt ggt gtg cca        624
Ala Leu Ala Ala Ala Glu Val Ala Phe Met Ile His Gly Gly Val Pro
        195                 200                 205 caa cgc agg gga cta cac ttt gct gta gca cca gag cag ccg ccg cca        672
Gln Arg Arg Gly Leu His Phe Ala Val Ala Pro Glu Gln Pro Pro Pro
    210                 215                 220 ata tcc aac cca aca cca gtc tga                                         696
Ile Ser Asn Pro Thr Pro Val
225                 230
```

<210> SEQ ID NO 4
<211> LENGTH: 231
<212> TYPE: PRT
<213> ORGANISM: Brassica napus

<400> SEQUENCE: 4

```
Glu Glu Glu Pro Leu Leu Gln Ser Val Glu Cys Arg Ile Cys Gln Glu
 1               5                  10                  15

Glu Asp Ile Thr Lys Asn Leu Glu Thr Pro Cys Ala Cys Asn Gly Ser
            20                  25                  30

Leu Lys Tyr Ala His Arg Lys Cys Val Gln Arg Trp Cys Asn Glu Lys
        35                  40                  45

Gly Asp Ile Ile Cys Glu Ile Cys His Gln Pro Tyr Gln Ser Gly Tyr
    50                  55                  60

Thr Ala Pro Pro Pro Pro Pro Pro Asp Glu Thr Ile Ile His Ile Gly
 65                  70                  75                  80

Asp Asp Trp Glu Asp Gly Val His Leu Asp Ser Ser Asp Pro Arg Ile
                 85                  90                  95
```

```
Leu Ala Met Ala Ala Glu Arg His Phe Leu Glu Ala Asp Tyr Asp
            100                 105                 110
Glu Tyr Ser Glu Ser Asn Ser Gly Ala Ala Phe Cys Arg Ser Ala
        115                 120                 125
Ala Leu Ile Leu Met Ala Leu Leu Leu Arg Asp Ala Leu Asn Leu
    130                 135                 140
Thr Thr Asn Pro Asp Asp Glu Asp Pro Thr Ala Phe Phe Ser Leu
145                 150                 155                 160
Phe Leu Leu Arg Ala Ala Gly Phe Leu Leu Pro Cys Tyr Ile Met Ala
                165                 170                 175
Trp Ala Ile Gly Ile Leu Gln Arg Arg Gln Arg Gln Glu Ala Ala
            180                 185                 190
Ala Leu Ala Ala Ala Glu Val Ala Phe Met Ile His Gly Gly Val Pro
        195                 200                 205
Gln Arg Arg Gly Leu His Phe Ala Val Ala Pro Glu Gln Pro Pro Pro
    210                 215                 220
Ile Ser Asn Pro Thr Pro Val
225                 230

<210> SEQ ID NO 5
<211> LENGTH: 852
<212> TYPE: DNA
<213> ORGANISM: Artificial Sequence
<220> FEATURE:
<223> OTHER INFORMATION: sequence of genes which increase tolerance of
      plants and microbes to abiotic stresses after base deletion and
      replacement
<220> FEATURE:
<221> NAME/KEY: CDS
<222> LOCATION: (1)..(852)

<400> SEQUENCE: 5 atg gct gat gat ttc agt tta tgt acc gat cgt ctg ata acg gcc gag     48
Met Ala Asp Asp Phe Ser Leu Cys Thr Asp Arg Leu Ile Thr Ala Glu
1               5                   10                  15 agc ttg gaa tca gaa aag gat tct gga gaa agt tcc agg ctt caa ggc     96
Ser Leu Glu Ser Glu Lys Asp Ser Gly Glu Ser Ser Arg Leu Gln Gly
            20                  25                  30 aaa gat gtg gct tct tct tca tct gcg gat gaa gct gaa gat gct agg    144
Lys Asp Val Ala Ser Ser Ser Ser Ala Asp Glu Ala Glu Asp Ala Arg
        35                  40                  45 aag tac tat gct gtt gtt gca gaa gag gag ccg ctt ctg caa tct gtt    192
Lys Tyr Tyr Ala Val Val Ala Glu Glu Glu Pro Leu Leu Gln Ser Val
    50                  55                  60 gag tgc cgt att tgc cag gag gaa gat atc act aag aac ttg gag act    240
Glu Cys Arg Ile Cys Gln Glu Glu Asp Ile Thr Lys Asn Leu Glu Thr
65                  70                  75                  80 cct tgt gct tgc aat ggc agt ttg aag tat gct cac cgc aag tgt gtt    288
Pro Cys Ala Cys Asn Gly Ser Leu Lys Tyr Ala His Arg Lys Cys Val
                85                  90                  95 cag cgt tgg tgt aat gag aaa ggc gac ata atc tgc gaa ata tgc cac    336
Gln Arg Trp Cys Asn Glu Lys Gly Asp Ile Ile Cys Glu Ile Cys His
            100                 105                 110 cag cct tat caa tct gga tat aca gca cct cca cct cct cct cct gat    384
Gln Pro Tyr Gln Ser Gly Tyr Thr Ala Pro Pro Pro Pro Pro Pro Asp
        115                 120                 125 gaa act ata att cac att ggt gac gac tgg gag gat gga gtt cac ttg    432
Glu Thr Ile Ile His Ile Gly Asp Asp Trp Glu Asp Gly Val His Leu
    130                 135                 140 gac tcg agc gac ccg cgc att cta gca atg gct gcg gcg gaa cga cat    480
Asp Ser Ser Asp Pro Arg Ile Leu Ala Met Ala Ala Ala Glu Arg His
```

```
                       145                 150                 155                 160
ttc ttg gaa gct gac tat gac gag tac tct gag tct aac tct agc ggt          528
Phe Leu Glu Ala Asp Tyr Asp Glu Tyr Ser Glu Ser Asn Ser Ser Gly
                       165                 170                 175 gct gcc ttc tgt cgc tct gct gct ctc atc ctg atg gca ctt tta ctg          576
Ala Ala Phe Cys Arg Ser Ala Ala Leu Ile Leu Met Ala Leu Leu Leu
                       180                 185                 190 tta cgt gat gca cta aac ctc aca act aac cca gat gac gag gac gat          624
Leu Arg Asp Ala Leu Asn Leu Thr Thr Asn Pro Asp Asp Glu Asp Asp
                       195                 200                 205 ccc act gcc ttc ttc tct ctt ttc ctt ctt cgt gct gct ggt ttt ctc          672
Pro Thr Ala Phe Phe Ser Leu Phe Leu Leu Arg Ala Ala Gly Phe Leu
                       210                 215                 220 ctc cca tgt tat atc atg gca tgg gcc atc ggt att ctc cag cgc cgg          720
Leu Pro Cys Tyr Ile Met Ala Trp Ala Ile Gly Ile Leu Gln Arg Arg
225                     230                 235                 240 agg caa aga cag gaa gca gct gcg cta gct gcg gcg gaa gtt gcc ttc          768
Arg Gln Arg Gln Glu Ala Ala Ala Leu Ala Ala Ala Glu Val Ala Phe
                       245                 250                 255 atg ata cac ggt ggt gtg cca caa cgc agg gga cta cac ttt gct gta          816
Met Ile His Gly Gly Val Pro Gln Arg Arg Gly Leu His Phe Ala Val
                       260                 265                 270 gca cca gag cag ccg ccg cca ata tcc aac cca aca                          852
Ala Pro Glu Gln Pro Pro Pro Ile Ser Asn Pro Thr
                       275                 280

<210> SEQ ID NO 6
<211> LENGTH: 284
<212> TYPE: PRT
<213> ORGANISM: Artificial Sequence
<220> FEATURE:
<223> OTHER INFORMATION: Synthetic Construct

<400> SEQUENCE: 6

Met Ala Asp Asp Phe Ser Leu Cys Thr Asp Arg Leu Ile Thr Ala Glu
1               5                   10                  15

Ser Leu Glu Ser Glu Lys Asp Ser Gly Glu Ser Ser Arg Leu Gln Gly
            20                  25                  30

Lys Asp Val Ala Ser Ser Ser Ala Asp Glu Ala Glu Asp Ala Arg
        35                  40                  45

Lys Tyr Tyr Ala Val Val Ala Glu Glu Glu Pro Leu Leu Gln Ser Val
    50                  55                  60

Glu Cys Arg Ile Cys Gln Glu Glu Asp Ile Thr Lys Asn Leu Glu Thr
65                  70                  75                  80

Pro Cys Ala Cys Asn Gly Ser Leu Lys Tyr Ala His Arg Lys Cys Val
                85                  90                  95

Gln Arg Trp Cys Asn Glu Lys Gly Asp Ile Ile Cys Glu Ile Cys His
            100                 105                 110

Gln Pro Tyr Gln Ser Gly Tyr Thr Ala Pro Pro Pro Pro Pro Asp
        115                 120                 125

Glu Thr Ile Ile His Ile Gly Asp Asp Trp Glu Asp Gly Val His Leu
    130                 135                 140

Asp Ser Ser Asp Pro Arg Ile Leu Ala Met Ala Ala Glu Arg His
145                 150                 155                 160

Phe Leu Glu Ala Asp Tyr Asp Glu Tyr Ser Glu Ser Asn Ser Ser Gly
                165                 170                 175

Ala Ala Phe Cys Arg Ser Ala Ala Leu Ile Leu Met Ala Leu Leu Leu
            180                 185                 190
```

```
Leu Arg Asp Ala Leu Asn Leu Thr Thr Asn Pro Asp Glu Asp Asp
        195                 200                 205

Pro Thr Ala Phe Phe Ser Leu Phe Leu Leu Arg Ala Ala Gly Phe Leu
    210                 215                 220

Leu Pro Cys Tyr Ile Met Ala Trp Ala Ile Gly Ile Leu Gln Arg Arg
225                 230                 235                 240

Arg Gln Arg Gln Glu Ala Ala Ala Leu Ala Ala Ala Glu Val Ala Phe
                245                 250                 255

Met Ile His Gly Gly Val Pro Gln Arg Arg Gly Leu His Phe Ala Val
            260                 265                 270

Ala Pro Glu Gln Pro Pro Pro Ile Ser Asn Pro Thr
        275                 280

<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
atgtcggatc atttgagttt atg                                       23

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
tcagactggt gttgggttgg atat                                      24

<210> SEQ ID NO 9
<211> LENGTH: 32
<212> TYPE: DNA
<213> ORGANISM: Artificial Sequence
<220> FEATURE:
<223> OTHER INFORMATION: Synthetic Construct

<400> SEQUENCE: 9
cgcggatcca tgtcggatca tttgagttta tg                             32

<210> SEQ ID NO 10
<211> LENGTH: 33
<212> TYPE: DNA
<213> ORGANISM: Artificial Sequence
<220> FEATURE:
<223> OTHER INFORMATION: Synthetic Construct

<400> SEQUENCE: 10
ccggagctct cagactggtg ttgggttgga tat                            33

<210> SEQ ID NO 11
<211> LENGTH: 32
<212> TYPE: DNA
<213> ORGANISM: Artificial Sequence
<220> FEATURE:
<223> OTHER INFORMATION: Synthetic Construct

<400> SEQUENCE: 11
cgcggatcca tgtcggatca tttgagttta tg                             32

<210> SEQ ID NO 12
```

```
<211> LENGTH: 33
<212> TYPE: DNA
<213> ORGANISM: Artificial Sequence
<220> FEATURE:
<223> OTHER INFORMATION: Synthetic Construct

<400> SEQUENCE: 12
ccggagctct cagactggtg ttgggttgga tat                              33

<210> SEQ ID NO 13
<211> LENGTH: 32
<212> TYPE: DNA
<213> ORGANISM: Artificial Sequence
<220> FEATURE:
<223> OTHER INFORMATION: Synthetic Construct

<400> SEQUENCE: 13
ccggagctca tgtcggatca tttgagttta tg                               32

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14
cgcggatcct cagactggtg ttgggttgga tat                              33

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
atttcatttg gagagaacac gg                                          22

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
tcagactggt gttgggttgg atat                                        24

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
atttcatttg gagagaacac gg                                          22

<210> SEQ ID NO 18
<211> LENGTH: 23
<212> TYPE: DNA
<213> ORGANISM: Artificial Sequence
<220> FEATURE:
<223> OTHER INFORMATION: Synthetic Construct

<400> SEQUENCE: 18
```

```
atgtcggatc atttgagttt atg                                            23
```

\<210\> SEQ ID NO 19
\<211\> LENGTH: 32
\<212\> TYPE: DNA
\<213\> ORGANISM: Artificial Sequence
\<220\> FEATURE:
\<223\> OTHER INFORMATION: Synthetic Construct

\<400\> SEQUENCE: 19

```
ccggaattca tgtcggatca tttgagttta tg                                  32
```

\<210\> SEQ ID NO 20
\<211\> LENGTH: 32
\<212\> TYPE: DNA
\<213\> ORGANISM: Artificial Sequence
\<220\> FEATURE:
\<223\> OTHER INFORMATION: Synthetic Construct

\<400\> SEQUENCE: 20

```
gctctagatc agactggtgt tgggttggat at                                  32
```

\<210\> SEQ ID NO 21
\<211\> LENGTH: 26
\<212\> TYPE: DNA
\<213\> ORGANISM: Artificial Sequence
\<220\> FEATURE:
\<223\> OTHER INFORMATION: Synthetic Construct

\<400\> SEQUENCE: 21

```
atggctgatg atttcagttt atgtac                                         26
```

\<210\> SEQ ID NO 22
\<211\> LENGTH: 25
\<212\> TYPE: DNA
\<213\> ORGANISM: Artificial Sequence
\<220\> FEATURE:
\<223\> OTHER INFORMATION: Synthetic Construct

\<400\> SEQUENCE: 22

```
ttgggttgga tattggcggc ggctg                                          25
```

\<210\> SEQ ID NO 23
\<211\> LENGTH: 35
\<212\> TYPE: DNA
\<213\> ORGANISM: Artificial Sequence
\<220\> FEATURE:
\<223\> OTHER INFORMATION: Synthetic Construct

\<400\> SEQUENCE: 23

```
ccggaattca tggctgatga tttcagttta tgtac                               35
```

\<210\> SEQ ID NO 24
\<211\> LENGTH: 34
\<212\> TYPE: DNA
\<213\> ORGANISM: Artificial Sequence
\<220\> FEATURE:
\<223\> OTHER INFORMATION: Synthetic Construct

\<400\> SEQUENCE: 24

```
ccggagctct tgggttggat attggcggcg gctg                                34
```

IOSLATED TT1 POLYNUCLEOTIDE, ENCODED PROTEINS AND VECTORS FOR INCREASING TOLERANCE OF PLANTS AND MICROBES TO ABIOTIC STRESSES AND THE USE THEREOF

TECHNICAL FIELD

The present invention belongs to molecular biology field, and specifically, relates to a new gene, the polypeptide encoded by the gene, the recombinant vector containing the gene and the use thereof for improving tolerance of plants and microbes to abiotic stresses.

BACKGROUND ART

With rapid development of molecular biology and constant improvement of genetic cloning technology, studies on genetic engineering for plants and microbes are being developed in depth and breadth, and researches on resistance genes have been transferred from tolerance to biotic stresses (e.g. disease, pest) to tolerance to abiotic stresses, such as drought, acid-alkaline, saline-alkaline and heat.

Because of the increased $CO_2$ emission, greenhouse effect on the earth is growing worse and leading to global warming. It is estimated that the global average temperature will increase by 1.4-5.8° in the next 100 years. Global warming gradually deteriorates the agricultural ecological environment. It is predicted that climate warming may lead to 17% of crop yield reduction. One research from IRRI (International Rice Research Institute) proved that during 1998-2003, the crop yield was decreased by 10% with the temperature elevated by 1°. In China, experts believe that by 2050, the nationwide average temperature will increase by 2.2°. Plants growing under natural conditions are all affected by the elevated temperature and grow more slowly. Some major crops, such as rice and corn, are especially easy to be influenced by hot weather during heading and filling stage, and result in crop yield reduction. On the other hand, according to FAO (Food and Agriculture Organization of the United Nations), the world population will exceed 10 billions by 2050. With further increased world population, there will be more and more pressure on agriculture, and worldwide food shortage will be a long-lasting problem. Being affected by global warming, lots of herbaceous plants will grow more slowly and even die, thus breaking ecosystem balance. Therefore, scientists all over the world are taking great efforts in searching for heat-tolerance relevant plant genes. So far from now, only a few heatshock protein genes and transcription factors thereof are found to be relevant with heat tolerance, while none of a single gene was reported to be capable of increasing heat tolerance of bacteria and plants.

Nowadays, there are 1 billion $hm^2$ of saline-alkaline land, which is about 10% of global arable areas, in more than 100 nations in the world. China alone has 99.13 millions $hm^2$ of saline-alkaline land, mainly at arid and semiarid regions of the north, northwest and northeast of China. There are more than 3.70 millions of $hm^2$ of saline-alkaline land at Songnenpingyuan at the western part of northeast China, which is one of the three major centralized areas of soda saline-alkaline land. Meanwhile, the areas of secondary salinization land are increasing rapidly due to the industrial pollution, the irrational irrigation and the ill use of chemical fertilizers. Saline-alkaline land affects the vegetation growth by reducing or even terminating the crop output, and it also indirectly deteriorates the ecological environment and corrodes engineering installations, which leads to 2.511 billion yuan of losses every year. Therefore, it is one of the problems that demand urgent solution in sustainable development of agriculture to reduce damages of soil salination to crops and make full use of the limited land resource. Besides of the comprehensive treatment by traditional physical, chemical and biological ways, etc., it will be one of the most cost-effective methods for enhancing tolerance of plants to stresses by genetic engineering with the up-to-date molecular biology method.

Saline-alkaline soil is the soil that contains too many salts of NaCl, $Na_2SO_4$, $Na_2CO_3$ and $NaHCO_3$. Damages of saline-alkaline soil towards plants mainly include complexed damages from stresses of salinity, high-pH and the interaction thereof. Damages from saline-alkaline stress are mainly represented in three ways: first, the massive accumulation of metal ions (mainly Na) in cytoplasm, which breaks the ionic balance and inhibits physiological and biochemical metabolic processes in cells, thus weakening the photosynthesis ability of plants and finally killing them with carbon starvation; second, the high osmotic circumstance of saline-alkaline soil, which may stop plant root systems from absorbing water, thus causing plants to die from "drought"; third, the relatively high pH value of saline-alkaline soil, which disturbs the acid-base balance between plants and the external environment, thus disrupting the membrane structure of cells and killing plants with exosmosis of cell content. Therefore, plants under saline-alkaline stresses need, on one hand, to reduce ion accumulation in cytoplasm; on the other hand, to generate from accumulation process some special products, such as proteins, amino acids and sugars, to increase osmosis of the cell, thus preventing water losses and stabilizing structures of plasma membrane and enzymes.

Being widespread, saline-alkaline land is becoming a new hotspot of research. Studies now are mainly focused on how plants on saline-alkaline land respond to pH stress, whilst there is only preliminary exploration towards physiological characterization and gene expression. The major objects of the study are certain kinds of saline-alkaline tolerant plants, such as weeping bulrush (*Puccinellia tenuiflora*), chinensis (*Leymus chinensis*), sunflower (*Helianthus annuus*) and nitrebush (*Nitraria schoberi*). However, studies of plant response to high pH stress at the molecular level are processing slowly. There are demands in the art for the development of backup genes that can enhance the tolerance of plants to saline-alkaline stress, as well as methods for enhancing the tolerance of plants to saline-alkaline stress by genetic engineering techniques.

The environmental hydrogen potential is normally presented by the negative logarithm of hydrogen ion concentration, i.e., pH value. The environmental pH greatly affects the vital movement of microbes on that: pH variation changes the electric charge on the surface of microbes, thus affecting microbe absorption towards nutrients; pH can affect the ionotropy of organic compounds in culture medium besides of direct influences to microbe cells, thus affecting microbes indirectly, since most non-ionic compounds penetrate into cells more easily than ionic ones; only with optimum pHs can maximum activity of enzymes be achieved, and those unsuitable pHs decrease enzyme activities and therefore affect the biochemical processes in microbe cells; and, pHs of too high or too low will both reduce the tolerance of microbes to heat.

With the growth of microbes in substrates, the hydrogen ion concentration of substrates will be changed with metabolism. As environmental pH changes, growth of microbes is retarded, and pHs beyond the maximum or minimum of tolerance will lead to death of microbes. With rapid development of molecular biology and constant improvement of genetic cloning technology, microbes with resistance can be cultivated through engineering studies that are being developed in depth and breadth, the key point of which is to find tolerance genes of microbes to saline-alkaline stresses.

Water resource shortage is now a global problem that restricts the development of agriculture. According to statistics, there are about 43% of arable lands that are under stresses of drought and semi-drought. The drought stress not only severely affects the growth of crops and reduces the yield, but also limits the promotion of improved crop strains. Therefore, it is one of the hot issues to enhance the tolerance of crops to drought in modern agriculture studies.

Studies on drought tolerance of plants relate to many fields such as plant morphology, physiology and biochemistry as well as molecular biology. It has been paid close attention to studies on drought tolerance with the following aspects, namely, structure changes of plant root systems and leaf blades under drought conditions; relationship between abscisic acid (ABA) and stomatal closure; relationship between drought tolerance of plants and osmoregulation substances of small molecule compounds, such as mannitol, proline, betaine, trehalose, fructosan, inositol, polyamine, etc.; and effects of aquaporin, reactive oxygen removal and late embryogenesis abundant protein on drought tolerance of plants.

With the development of molecular biology research, some important drought tolerant genes are discovered and cloned one after another, and drought tolerant transgenic plants of tobacco and rice are obtained. Transgenic rice lines with drought tolerance have been successfully cultivated, which brought about broad utilization prospects on studies of drought tolerant genes of other plants. Now, there are mainly two strategies for cultivating drought tolerant species by genetic engineering techniques. One is to enhance the synthesis capacity of permeable metabolites of plants, which can therefore synthesize under water stresses more osmoregulation substances (e.g. mannitol, betaine, trehalose, etc.) to improve the osmoregulation, thus enhancing the drought tolerance of plants. The other is to enhance the ability of plants of clearing active oxygen radicals with over expression of certain enzymes (e.g. SOD, POD, CAT, etc.) under water stresses, thus getting rid of harmful active oxygen radicals effectively and enhancing the drought tolerance of plants. With osmoregulation as a main mechanism for the drought tolerance of plants, improvement for synthesis of proline and betaine has recently been achieved with plant genetic engineering method, and promising progresses have been made in the cultivation of drought tolerant transgenic plants largely based on osmoregulations.

Proline is an amino acid of great solubility. With dipolarity, proline connects proteins with its hydrophobic end and water molecules with hydrophilic end, thus binding more water molecules for proteins and increasing the solubility thereof to involve more soluble proteins in osmoregulations. Meanwhile, the improvement of bound water content may prevent or decrease protein denaturations caused by dehydration of cells. Therefore, the improvement of synthetic ability for proline may enhance the drought tolerance of plants, and some successful reports have been made in this respect.

All in all, it is recently a hotspot of improving plants with genetic engineering techniques, and it is one choice to enhance the plant tolerance to abiotic stresses and cultivate plant lines of resistance by genetic engineering techniques. However, there are seldom reports of a single gene that could comprehensively enhance various tolerances of plants and microbes to abiotic stresses.

DISCLOSURE OF THE INVENTION

The present invention aims at providing a gene capable of increasing tolerance of plants and microbes to abiotic stresses, a polypeptide encoded by the gene and a recombinant vector containing the gene. The present invention aims also at providing a transgenic method for plants or bacteria and method for detecting whether said gene is transformed into host.

Schemes of the present invention are as follows:

The gene of the present invention comprises the nucleotide sequence of SEQ ID NO: 1 in the sequence list.

Or, the gene of the present invention comprises derived sequences by substituting, deleting or adding one or more nucleotides of the nucleotide sequence of SEQ ID NO: 1, said derived sequences encoding polypeptides with the same function as that encoded by the sequence of SEQ ID NO: 1.

Wherein, the above-mentioned function is to increase the tolerance of plants or microbes to abiotic stresses.

Wherein, the above-mentioned tolerance to abiotic stresses is tolerance to at least one stress selected from drought, acid-alkaline, saline-alkaline and heat.

Furthermore, the above-mentioned gene comprises nucleotide sequence of SEQ ID NO: 5 in the sequence list.

The polypeptide of the present invention comprises:

(1) the amino acid sequence of SEQ ID NO: 2 in the sequence list; or (2) amino acid sequences derived from substitution, deletion or addition of at least one amino acid of the amino acid sequence in (1).

Wherein, the aforementioned polypeptide possesses with the function of increasing tolerance of plants or microbes to abiotic stresses. Said tolerance to abiotic stresses is tolerance to at least one stress selected from drought, acid-alkaline, saline-alkaline and heat.

The present invention provides genes encoding above-mentioned polypeptides, as well as monoclonal antibodies raised against the polypeptides.

The present invention also provides the use of aforementioned genes in increasing tolerance of plants and microbes to abiotic stresses, wherein said tolerance to abiotic stresses is tolerance to at least one stress selected from drought, acid-alkaline, saline-alkaline and heat. Of course, the polypeptide of the present invention may also be used to increase tolerance of plants and microbes to abiotic stresses.

To better realize the aforementioned use, the present invention also provides a recombinant vector, said recombinant vector comprising the aforementioned gene. Furthermore, the aforementioned recombinant vector may express the gene of the present invention. Furthermore, the aforementioned recombinant vector is a recombinant plasmid.

The present invention also provides a host cell comprising the above-mentioned recombinant vector, as well as transgenic plants or microbes containing the above-mentioned recombinant vector.

Based on the product and use as mentioned above, the present invention provides a plant transgenic method with following steps:

(1) operably-linking the aforementioned gene into the plant expression and regulation sequence on the expression vector to form a recombinant expression vector comprising nucleotide sequence of SEQ ID NO: 1;

(2) transforming the recombinant expression vector of step (1) into plant cells; and (3) selecting and obtaining transformed cells, followed by regenerating the transformed cells to form transgenic plants and the offspring thereof, said offspring including plant seeds as well as plant tissues.

Meanwhile, the present invention also provides a microbe transgenic method with following steps:

(1) operably-linking the aforementioned gene into the microbe expression and regulation sequence on the expression vector to form recombinant expression vector comprising nucleotide sequence of SEQ ID NO: 1;

(2) transforming the recombinant expression vector of step (1) into microbes; and (3) selecting and obtaining transformed microbes.

With above-mentioned methods, plants or microbes with enhanced tolerance to abiotic stresses may be prepared.

To better perform the above-mentioned technical schemes, the present invention also provides a method for detecting whether sequences of above-mentioned genes are comprised in samples. With said method, probes prepared according to target genes are hybridized with the sample, and the combination of sample and probe is detected. If the sample is combined to the probe, then said gene sequence of SEQ ID NO: 1 is comprised in the sample; wherein said sample is a PCR amplification product from the genome of the detected plant.

Furthermore, the above-mentioned PCR amplification primers correspond to the two sides or the middle of the nucleotide sequence of the above-mentioned gene, with primer length of 15-50 nucleotides.

Wherein, above-mentioned probes consist of 8-100 contiguous nucleotides of the nucleotide sequence of the target gene. Preferably, said probes consist of 15-50 contiguous nucleotides of the nucleotide sequence of target gene.

The present invention has beneficial results as follows. First, it provides the use of TT1 gene for enhancing drought tolerance of plants, wherein examples of the present invention have proved that the seed germination rate of plants with TT1 gene transformed and over-expressed was increased significantly in drought circumstances. Also increased is the proline content in plants after growth, and the growth status of seedlings thereof further proves that TT1 gene can enhance the drought tolerance of plants. The method for cultivating drought tolerant plants of the present invention is convenient and effective, thus providing a new choice for enhancing the saline-alkaline tolerance of plants, which possess with good utilization prospects.

DESCRIPTION OF DRAWINGS

FIG. 1-A: growth status photo of *E. coli* pET28 strain at 42°; FIG. 1-B: growth status photo of *E. coli* pET28 strain containing recombinant plasmid of SEQ ID NO: 1 at 42°; FIG. 1-C: growth status photo of both strains on the same plate at 42°.

FIG. 3-A: detection result of transgenic *Brassica napus* line with over-expressed SEQ ID NO: 1, wherein, M stands for marker, and 1, 2, 3 and 4 for transgenic *Brassica napus* line with over-expressed SEQ ID NO: 1; FIG. 3-B: detection result of Transgenic *Brassica napus* line with inhibit-expressed SEQ ID NO: 1, wherein, M stands for marker, and 1 and 2 for transgenic *Brassica napus* line with inhibit-expressed SEQ ID NO: 1. As shown, the size of target band detected is identical with that of SEQ ID NO: 1 as anticipated, which is about 860 bp.

Wherein, FIG. 4-A: growth status photos of transgenic and non-transgenic *Brassica napus* at normal growth temperature (22°), and as shown, transgenic and non-transgenic *Brassica napus* both grow normally; FIG. 4-B: growth status photos of transgenic and non-transgenic *Brassica napus* with elevated temperature of 34° for 3 days, and as shown, transgenic *Brassica napus* line with over-expressed SEQ ID NO: 1 (Zn-OE) grows normally, while non-transgenic *Brassica napus* (WT) grows slowly, and transgenic *Brassica napus* line with inhibit-expressed SEQ ID NO: 1 (Zn-DN) grows more slowly; FIG. 4-C: growth status photos of transgenic and non-transgenic *Brassica napus* with elevated temperature of 34° for 5 days, and as shown, transgenic *Brassica napus* line with over-expressed SEQ ID NO: 1 (Zn-OE) grows normally, while both *Brassica napus* (WT) and transgenic *Brassica napus* line with inhibit-expressed SEQ ID NO: 1 (Zn-DN) have died.

FIG. 5 shows photos comparing heat tolerance among transgenic *Brassica napus* with over- and inhibit-expressed SEQ ID NO: 1 and non-transgenic *Brassica napus*, all being treated at 34° for 3-5 days. FIG. 5-A: growth status photos of 3 kinds of plants treated at 34° for 3 days, and as shown, transgenic *Brassica napus* with over-expressed SEQ ID NO: 1 (Zn-OE) grows normally, *Brassica napus* (WT) grows slowly with yellow and curved leaf blades, and transgenic *Brassica napus* with inhibit-expressed SEQ ID NO: 1 (Zn-DN) turns yellow with significant curved leaf blades and stopped growth; FIG. 5-B: growth status photos of 3 kinds of plants treated at 34° for 5 days, and as shown, transgenic *Brassica napus* with over-expressed SEQ ID NO: 1 (Zn-OE) grows normally, while both transgenic *Brassica napus* with inhibit-expressed SEQ ID NO: 1 (Zn-DN) and *Brassica napus* (WT) have died.

FIG. 6 shows photos comparing the expression difference of SEQ ID NO: 1 at transcription level among transgenic *Brassica napus* with over- and inhibit-expressed SEQ ID NO: 1 and non-transgenic *Brassica napus*. As shown, in *Brassica napus* with over-expressed SEQ ID NO: 1 (Zn-OE), SEQ ID NO: 1 gene expression is increased to 2.5-folds of that in non-transgenic *Brassica napus*; whilst in *Brassica napus* with inhibit-expressed SEQ ID NO: 1 (Zn-DN), SEQ ID NO: 1 gene expression is decreased to only half of that in wild type *Brassica napus* (WT).

FIG. 7 shows the induced expression of pGEX-2T (GTK-Zn) recombinant plasmid comprising SEQ ID NO: 1 in *E. coli*, wherein, 1: GTK (empty vector pGEX-2T) expressed in *E. coli*; 2: Marker; 3-7: GTK-Zn (recombinant protein plasmid comprising SEQ ID NO: 1) expressed in *E. coli*; 3, 4: IPTG induction for 2 hours; 5, 6: IPTG induction for 3 hours; 7: IPTG induction for 4 hours. The black arrow illustrates that the protein expressed is 58 KD. As shown, in *E. coli*, the induced expression of pGEX-2T recombinant plasmid comprising sequence of SEQ ID NO: 1 (GTK-Zn) results in identical protein band as anticipated (58 KD).

FIG. 8-A: growth status photo of *E. coli* containing pET28 at 42°; FIG. 8-B: growth status photo of *E. coli* containing recombinant plasmid of SEQ ID NO: 4 at 42°.

EMBODIMENTS OF THE INVENTION

Figure 1:
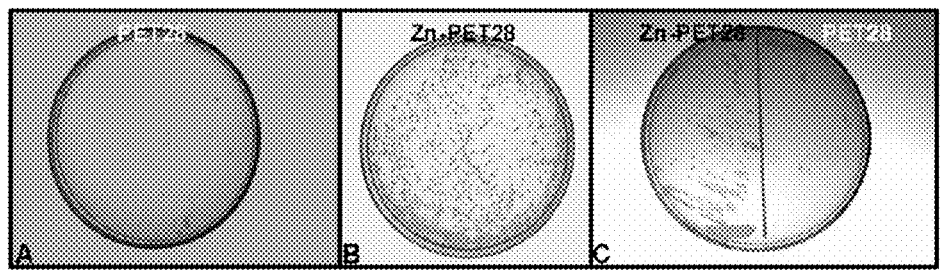
FIG. 1 shows growth status photos of *E. coli* containing recombinant plasmid of SEQ ID NO: 1 and that containing pET28 (*E. coli* pET28) at 42°.

Said gene of the present invention comprises substantially the nucleotide sequence of SEQ ID NO: 1 in the sequence list. It derives from the plant *Brassica napus*, which belongs to *Brassica* genus of Brassicaceae (also known as Cruciferae) family. The nucleotide sequence of SEQ ID NO: 1 in the sequence list is obtained by steps as follows: selecting and obtaining one EST sequence in *Brassica napus* by using yeast two-hybrid method with atp6 gene of *Brassica napus* as a bait protein; followed by obtaining the nucleotide sequence of SEQ ID NO: 1 in the sequence list by the method of 5'RACE according to the selected sequence. Then, a pair of PCR primers is designed according to the nucleotide sequence of SEQ ID NO: 1, which is then amplified from *Brassica napus* cDNA.

Said recombinant vector of the present invention is obtained by inserting TT1 gene into a vector, and said vector may be selected from various vectors known in the art, especially from eucaryotic expression vectors (e.g. pBI121 or pCAMBIA2301). Said recombinant vector is used to transform host cells or microbes in the present invention, including procaryotic and eucaryotic hosts. Commonly used eucaryotic hosts include yeasts and other plant cells, and commonly used procaryotic host is *E. coli*.

Said polypeptide enhancing heat tolerance of plants and microbes in the present invention comprises the amino acid sequence of SEQ ID NO: 2 in the sequence list; or sequences derived by substituting, deleting or adding one or more amino acids of the amino acid sequence of SEQ ID NO: 2, which possess the same function as that of SEQ ID NO: 2.

Said "operably-linked" in the present invention means that certain parts of linear DNA sequence can influence activities of the other parts on the same linear DNA sequence. For example, if a signal peptide DNA is expressed as a precursor and participates the secretion of a polypeptide, then the signal peptide (that secretes leading sequence) DNA is operably-linked to the polypeptide DNA; if a promoter controls the transcription of a sequence, then it is operably-linked to the coding sequence; and if a ribosome binding site is placed at a position that it could be translated, then it is operably-linked to a coding sequence. Generally speaking, "operably-linked" means being contiguous, and for the secretion of leading sequence it means being contiguous in reading frames.

In one example of the present invention, recombinant plasmid in step (1) is transformed into *Agrobaterium*, and the *Agrobaterium* containing recombinant plasmid is co-cultivated with eucaryotic host cells at 22-28° in dark for 1-2 days, followed by obtaining transformed cells comprising SEQ ID NO: 1 through screenings (e.g. antibiotic screening) as well as regenerating transgenic plants and the offspring thereof.

In the present invention, "SEQ ID NO: 1" means a nucleotide sequence encoding polypeptide that possesses with the function of the protein of SEQ ID NO: 1, and the degenerate sequences thereof. Said degenerate sequences are sequences with one or more codons being substituted by degenerate codons encoding the same amino acid. Because of the codon degeneracy, a degenerate sequence that has as low as 89% of homology with SEQ ID NO: 1 can encode the sequence encoded by SEQ ID NO: 1. The term also includes nucleotide sequences that can hybridize with SEQ ID NO: 1 under moderate stringent conditions, preferably under high stringent conditions. The term also includes nucleotide sequences exhibiting at least 80%, more preferably at least 90%, and most preferably at least 95% of homology to the nucleotide sequence of SEQ ID NO: 1. The same function in the present invention means increasing drought tolerance of plants.

The term also includes variants of the open reading frame sequence of SEQ ID NO: 1 that can encode proteins having the same function as natural SEQ ID NO: 1 does. Such variants include (but not limit to): deletion, insertion and/or substitution of several nucleotides (normally 1-90, preferably 1-60, more preferably 1-20 and most preferably 1-10), as well as addition at 5' and/or 3' terminals of several nucleotides (normally less than 60, preferably less than 30, more preferably less than 10 and most preferably less than 5).

In the present invention, a protein or polypeptide of SEQ ID NO: 2 means a polypeptide having activities of the protein encoded by SEQ ID NO: 1. Such variants include, but not limit to, deletion, insertion and/or substitution of several amino acids (normally 1-50, preferably 1-30, more preferably 1-20 and most preferably 1-10), as well as addition at C and/or N terminals of several amino acids (normally less than 20, preferably less than 10 and more preferably less than 5). For example, in said proteins, substitution by amino acid with similar properties usually does not change the function of the protein. Another example is that the addition at C and/or N terminals of one or more amino acids usually does not change the protein function, either. Said term also includes active fragments and derivatives of the protein of SEQ ID NO: 2.

Variants of the SEQ ID NO: 2 polypeptide of the present invention include: homologous sequences, conserved variants, allelic variants, natural mutants, induced mutants, proteins encoded by DNAs that can hybridize with SEQ ID NO: 1 under high or low stringent conditions, and polypeptides or proteins obtained from the use of antiserum against the polypeptide of SEQ ID NO: 2. The present invention also provides other polypeptides, such as fusion proteins comprising the polypeptide of SEQ ID NO: 2 or fragments thereof. Besides of polypeptides with substantially the full length, the present invention also includes soluble fragments of the polypeptide of SEQ ID NO: 2, which may consist of at least about 10, normally at least about 30, preferably at least about 50, more preferably at least about 80 and most preferably at least about 100 of contiguous amino acids of the polypeptide sequence of SEQ ID NO: 2.

In the present invention, "polypeptide with conserved variation of SEQ ID NO: 2" means a polypeptide which, compared with the amino acid sequence of SEQ ID NO: 2, has at the most 10, preferably at the most 8 and more preferably at the most 5 of amino acids substituted by those with similar properties. Such polypeptide with conserved variation is obtained most preferably from substitutions according to Table 1.

TABLE 1

Substitutions of amino acids

| Initial residues | Representative substitutions | Preferably substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also includes analogues of the protein or polypeptide of SEQ ID NO: 2. Differences of such analogues with natural polypeptide of SEQ ID NO: 2 may be in amino acid sequence, or in modifications that will not change the sequence, or both. Such polypeptides include natural or induced genetic variants. The induced variants could be obtained with various techniques, such as random mutagenesis by radiation or exposing on mutagens, as well as site-directed mutagenesis or other known molecular biology techniques. Said analogues also include those comprising residues different from natural L-amino acids (e.g. D-amino acids), and those comprising non-naturally existed or synthetic amino acids (e.g. β, γ-amino acids). It should be appreciated that polypeptides of the present invention are not limited to the above-mentioned exemplary representative ones.

The modification (normally without changing the primary structure) includes chemical derivatization of polypeptides in vivo or in vitro, such as acetylation or carboxylation. The modification also includes glycosylation, such as those polypeptides produced from glycosylation in polypeptide synthesis and processing or reprocessing steps, which could be achieved by exposing polypeptide onto enzymes performing glycosylation (e.g. glycosylase or deglycosylase of mammalian animals). The modification also includes sequences comprising phospho-amino acid residues (e.g. phosphotyrosine, phosphoserine, phosphothreonine). Also included are polypeptides modified to have the property of enhanced proteolysis resistance or improved solubility.

Also, the expression of SEQ ID NO: 1 gene product may be assayed with northern blotting, which detects whether RNA transcription exists in cells and the amount thereof Northern blotting analysis of SEQ ID NO: 1 RNA and Western blotting analysis of SEQ ID NO: 2 specific antibodies may be combined to verify the expression of SEQ ID NO: 1 in biospecimens.

In addition, based on the homology of nucleic acids and expressed proteins, homologous genes or proteins of SEQ ID NO: 1 may be screened according to the nucleotide and amino acid sequence of the present invention.

To obtain *Brassica napus* cDNA lattices relating to SEQ ID NO: 1 gene, DNA probes may be used to screen the *Brassica napus* cDNA library, said probes being obtained from radioactively labeling the nucleotide sequence of SEQ ID NO: 1, entirely or partially, with $^{32}P$ under low stringent conditions. The cDNA library most suitable for screening is that from *Brassica napus*. Methods for constructing cDNA libraries from cells or tissues of interest are well known in the art of molecular biology. Moreover, many of these cDNA libraries may be purchased, for example, from Clontech, Stratagene, Palo Alto, Calif. Nucleotide sequences of gene families related to SEQ ID NO: 1 may be identified with such screening methods.

Once being obtained, the relevant sequence may be produced in great amounts by recombinant technique, in which it is usually cloned into vectors, followed by transforming cells, and then the relevant sequence is separated from propagated host cells by routine methods.

The present invention will now be illustrated with reference to the following examples, wherein experiments are performed according to, if not marked out, routine conditions known by those skilled in the art, such as in Sambrook and Russell, *Molecular Cloning: A Laboratory Manual*. (New York: Cold Spring Harbor Laboratory Press, 1989), or conditions suggested by manufacturers. In the following examples, vectors pET28, pGEX-2T, pGEM-T and strain BL21 are purchased from Qiagen corp., and strain EHA105 and vector pBI121 from Clontech corp. Other chemicals are purchased with analytical pure. In the following examples, "SEQ ID NO: 1", while being used alone, can be appreciated by those skilled in the art as the abbreviation of "nucleotide sequence of SEQ ID NO: 1"; and "SEQ ID NO: 4" alone as the abbreviation of "nucleotide sequence of SEQ ID NO: 4".

EXAMPLE 1

Cloning and Obtaining of a New Gene of the Present Invention

One EST sequence (as shown in SEQ ID NO: 3, which encodes the amino acid sequence of SEQ ID NO: 4) in *Brassica napus* was selected according to yeast two-hybrid method (refer to publications of Clontech corp.), with the atp6 gene (genebank gi: 89279377) of *Brassica napus* as a bait protein. Then, said gene of the present invention comprising the nucleotide sequence of SEQ ID NO: 1 in the sequence list was obtained by the method of 5'RACE (refer to publications of TaKaRa corp.) according to the selected sequence. Primers were designed according to the nucleotide sequence of SEQ ID NO: 1, with

```
upstream primer (SEQ ID NO: 7):
5'-ATGTCGGATCATTTGAGTTTATG-3',
and downstream primer (SEQ ID NO: 8):
5'-TCAGACTGGTGTTGGGTTGGATAT-3'.
```

Then the nucleotide sequence of SEQ ID NO: 1 was amplified by PCR from *Brassica napus* cDNA.
PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (refer to the manual of PCR product purification of Qiagen corp.) and sequenced to obtain gene fragments of the sequence of SEQ ID NO: 1.

EXAMPLE 2

Construction of *E. coli* Expressing SEQ ID NO: 1

1. Construction of Recombinant Plasmid and Molecular Verification
Primers were designed according to the nucleotide sequence of SEQ ID NO: 1, with

```
upstream primer (SEQ ID NO: 9):
5'-CGCGGATCCATGTCGGATCATTTGAGTTTATG-3',
and downstream primer (SEQ ID NO: 10):
5'-CCGGAGCTCTCAGACTGGTGTTGGGTTGGATAT-3'.
```

Then the nucleotide sequence of SEQ ID NO: 1 was amplified by PCR from *Brassica napus* cDNA.
PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (refer to the manual of PCR product purification kit of Qiagen corp.), then digested with BamH1 and Sac1, recovered from gel and ligated into procaryotic expression vector PET28 (ligation sites: BamH1 and Sac1) to obtain recombinant plasmid comprising sequence of SEQ ID NO: 1. Then *E. coli* was transformed with the recombinant plasmid and plated onto LB agar containing Amp. The *E. coli* pET28 strain containing recombinant plasmid of SEQ ID NO: 1 was obtained after sequencing.

EXAMPLE 3

Experiment of Heat Tolerance of *E. coli* Expressing SEQ ID NO: 1

Verification of heat tolerance of *E. coli* pET28 strain containing recombinant plasmid of SEQ ID NO: 1: *E. coli* pET28 strain containing recombinant plasmid of SEQ ID NO: 1 and *E. coli* pET28 host strain, both with OD value of 0.3, were plated onto LB agar with inoculation amount of 1%, respectively, and cultured overnight at 42°. The experiment showed that *E. coli* pET28 host strain could not grow after being treated at 42° (see FIG. 1-A); while *E. coli* pET28 strain containing recombinant plasmid of SEQ ID NO: 1 grew well at 42° (see FIG. 1-B).

Figure 2:
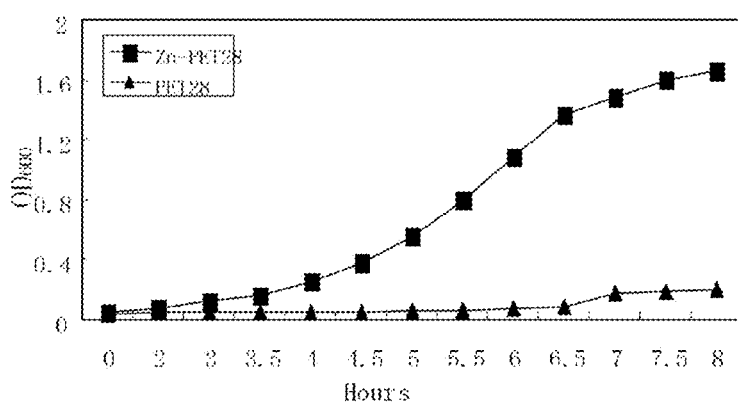
FIG. 2 shows a diagram comparing growth curves of *E. coli* containing recombinant plasmid of SEQ ID NO: 1 and that containing pET28 (*E. coli* pET28) at the growth condition of 44°, wherein squares stand for the growth curve of *E. coli* pET28 strain containing recombinant plasmid of SEQ ID NO: 1 (abbr. Zn-PET28) at 44°, which was showed to grow normally at 44°; and triangles stand for the growth curve of *E. coli* pET28 strain (abbr. PET28) at 44°, showing that such a strain can not grow at 44°.

Growth status of *E. coli* pET28 strain containing recombinant plasmid of SEQ ID NO: 1 was compared with that of *E. coli* pET28 host strain at 44° according to the above-mentioned operation. The experiment showed that the growth curve of *E. coli* pET28 strain containing recombinant plasmid of SEQ ID NO: 1 showed a logarithmic growth (see FIG. 2, Zn-pET28), illustrating a normal growth at 44°; while *E. coli* pET28 host strain could not grow at the temperature of 44° (see FIG. 2, pET28).

The results showed that *E. coli* pET28 strain containing recombinant plasmid of SEQ ID NO: 1 possessed with heat tolerance.

EXAMPLE 4

Expression of SEQ ID NO: 1 in *Brassica napus* Cells and Preparation of Transgenic Plants 1. Construction of Recombinant Plasmid with Over- and Inhibit-Expressed Target Gene
(1) Construction of Recombinant Plasmid with Over-Expressed Target Gene
Primers were designed according to the nucleotide sequence of SEQ ID NO: 1, with

```
upstream primer (SEQ ID NO: 11):
5'-CGCGGATCCATGTCGGATCATTTGAGTTTATG-3';
and downstream primer (SEQ ID NO: 12):
5'-CCGGAGCTCTCAGACTGGTGTTGGGTTGGATAT-3'.
```

The entire nucleotide sequence of SEQ ID NO: 1 was amplified by PCR from *Brassica napus* cDNA.
PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (see publications of Qiagen corp.), then digested with BamH1 and Sac1, recovered from gel and ligated into vector pBI121 (ligation sites: BamH1 and Sac1), to obtain the over-expressed recombinant plasmid comprising SEQ ID NO: 1, which was then transformed into *Agrobaterium*. And *Brassica napus* was then transformed by hypocotyl infection.

(2) Construction of Recombinant Plasmid with Inhibit-Expressed Target Gene

Primers were designed according to the nucleotide sequence of SEQ ID NO: 1, with

```
upstream primer (SEQ ID NO: 13):
5'-CCGGAGCTCATGTCGGATCATTTGAGTTTATG-3',
and downstream primer (SEQ ID NO: 14):
5'-CGCGGATCCTCAGACTGGTGTTGGGTTGGATAT-3'.
```

The entire nucleotide sequence of SEQ ID NO: 1 was amplified by PCR from *Brassica napus* cDNA.

PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (see publications of Qiagen corp.), then digested with BamH1 and Sac1, recovered from gel and ligated into vector pBI121 (ligation sites: BamH1 and Sac1), to obtain the inhibit-expressed recombinant plasmid comprising SEQ ID NO: 1, which was then transformed into *Agrobaterium*. And *Brassica napus* was then transformed by hypocotyl infection (see step 2).

2. Transformation of *Brassica napus* by Hypocotyl Infection (1) Obtaining Aseptic Seedlings Plump *Brassica napus* seeds were selected and vernalized overnight at 4° (synchronized germination), then immersed with 70% of ethanol for 30 s and 0.1% of mercuric chloride ($HgCl_2$) solution for 8-10 min, rinsed with sterile water for 5 times and dried with filter paper, and then plated onto MS agar medium. After cultivated at 24° for 2-3 days in a dark chamber, the culture was exposed to illumination for 16 h/d to continue germination. The hypocotyl of aseptic seedlings (in about 7-8 days) was taken with 5-7 cm as transformation acceptor.

(2) Pre-Culture of the Hypocotyl

The *Brassica napus* hypocotyl was sliced into sections of about 7 mm and well distributed onto pre-culture medium (MS+2 mg/L of 6-BA, 1 mg/L of 2,4-D, 2.5 mg/L of $AgNO_3$ and 19.62 mg/L of AS) to be pre-cultivated for 2-3 days (wherein the hypocotyl became coarse).

(3) Infection and Co-Cultivation of Hypocotyls

*Agrobaterium* containing recombinant plasmid comprising over- and inhibit-expressed SEQ ID NO: 1, respectively, were inoculated into LB medium containing 20 mg/L of Str, 50 mg/L of Kan and 40 mg/L of Rif and cultivated overnight at 28°, and cells were collected and resuspended with MS medium containing 100 mg/L AS till $OD_{600}$=0.4-0.6, followed by incubating at 28° for 1-2 h.

Pre-cultured healthy *Brassica napus* hypocotyls were immersed into bacteria liquid of *Agrobaterium* containing recombinant plasmid comprising over- and inhibit-expressed SEQ ID NO: 1, respectively, for 30 s-1 min, with constant oscillation to fully contact the bacteria liquid with hypocotyls. Spare bacteria liquid was quickly removed with aseptic filter paper. Then *brassica napus* hypocotyls were layed flat onto co-culture medium (MS+2 mg/L of 6-BA, 1 mg/L of 2,4-D, 2.5 mg/L of $AgNO_3$ and 19.62 mg/L of AS) to be co-cultivated for 2 d.

(4) Screening Culture and Germ Induction

The two of co-cultivated *brassica napus* hypocotyls were inoculated into differential medium (MS+2 mg/L of 6-BA, 1 mg/L of 2,4-D, 2.5 mg/L of $AgNO_3$ and 19.62 mg/L of AS) to continue the cultivation. Germ callus was obtained after 4 weeks of cultivation with the medium renewed by every 2 weeks.

(5) Radication

The germ was sliced from callus tissue and transferred onto radication medium (½ MS, 0.15 mg/L of NAA and 250 mg/L of Cef) after both germ callus had grown up with 4-6 pieces of euphylla on screening culture medium (MS+2 mg/L of 6-BA, 2.5 mg/L of $AgNO_3$, 500 mg/L of Carb and 10 mg/L of Kan). The culture tank was moved outdoors for 2-3 d after the root system of regenerated seedlings had grown well, followed by opening the tank and hardening seedlings for 2-3 d.

(6) Pot Culture

Transgenic plants comprising over- and inhibit-expressed SEQ ID NO: 1 were cultivated respectively on radication medium to develop the entire root system, and then transferred to pot culture.

(7) PCR Detection of Transgenic *Brassica napus*

Total DNA was extracted respectively from small amounts of leaves of the two regenerated plants that had grown well in soil. And PCR detection was performed with the DNA extracted as templates.

Detection of transgenic *Brassica napus* line with over-expressed target gene, with

```
upstream primer (SEQ ID NO: 15):
5' ATTTCATTTGGAGAGAACACGG 3',
and downstream primer (SEQ ID NO: 16):
5' TCAGACTGGTGTTGGGTTGGATAT 3'
```

PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 37 times |
| 6. 72° | 5 min (final elongation) |
| 7. Conservation at 4°. | |

Figure 3:
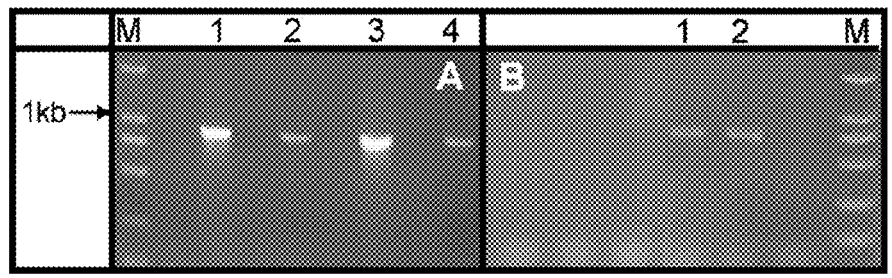
FIG. 3 shows photos of PCR detection results of transgenic *Brassica napus* lines with over- and inhibit-expressed SEQ ID NO: 1.

Then agarose electrophoresis was performed to detect the presence of target band, which was an indication that the target gene had been transformed into *Brassica napus*, see FIG. 3-A.

Detection of transgenic *Brassica napus* line with inhibit-expressed target gene, with

```
upstream primer (SEQ ID NO: 17):
5' ATTTCATTTGGAGAGAACACGG 3',
and downstream primer (SEQ ID NO: 18):
5' ATGTCGGATCATTTGAGTTTATG 3'
```

PCR procedure was as follows:

| | |
|---|---|
| 1. 95° | 4 min (pre-denaturation) |
| 2. 95° | 30 s (denaturation) |
| 3. 53° | 30 s (annealing) |

| | |
|---|---|
| 4. 72° | 50 s (elongation) |
| 5. Steps 2-4 | cycle for 37 times |
| 6. 72° | 5 min (final elongation) |
| 7. Conservation at 4°. | |

Then agarose electrophoresis was performed to detect the presence of target band, which was an indication that the target gene had been transformed into Brassica napus, see FIG. 3-B.

3. Detection of the SEQ ID NO: 1 Expression in Transgenic Brassica napus Plants by RT-PCR (1) Preparation and quantitation of RNAs of transgenic plants comprising over- and inhibit-expressed SEQ ID NO: 1 as well as non-transgenic Brassica napus: refer to Molecular Cloning: A Laboratory Manual (Sambrook et al., 1989).

(2) RNAs from transgenic plants comprising over- and inhibit-expressed SEQ ID NO: 1 as well as non-transgenic Brassica napus were reverse-transcripted into single-chain cDNAs, respectively.

2 ug total RNA of each of the 3 plant materials was denatured at 65° for 5 min. Substances were mixed into a 1.5 ml Eppendorf tube in the following order: heat-denatured RNA, 4 ul of 5×1st Strand Synthesis Buffer, 1 ul of DNTP, 1 ul of RNase Inhibitor, 1 ul of Oligo (dT) 18 (0.5 g/L), 1 ul of M-MLV and $H_2O$ to the volume of 20 ul. The solution was then mixed and incubated at 42° for 1 h.

(3) Semiquantitative PCR reaction

1) Determination of Template Amount

Firstly, PCR amplification was performed with reverse-transcripted single-chain cDNA as a template and actin gene as a internal parameter, wherein the amount of actin amplified from said 3 reverse-transcripted single-chain cDNAs were controlled identically (calculated from optical density value of the band from electrophoresis), thus further determining the template amount of single-chain cDNA needed.

PCR amplification procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 27 times |
| 6. 72° | 5 min (final elongation) |
| 7. Conservation at 4°. | |

2) Determination of Cycle Number

Genes of actin and SEQ ID NO: 1 were amplified with PCR using the 3 reverse-transcripted single-chain cDNAs, respectively, and sampled at cycles of 15, 18, 21, 24, 27 and 30 to determine exponential growth phase and plateau phase by electrophoresis. Semiquantitative PCR reaction of samples was carried out at exponential growth phase (21 cycles).

PCR amplification procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 21 times |
| 6. 72° | 5 min (final elongation) |
| 7. Conservation at 4°. | |

The result showed that, in transgenic Brassica napus with over-expressed SEQ ID NO: 1 (Zn-OE), SEQ ID NO: 1 gene expression was increased to 2.5-folds of that in control plant (Brassica napus, WT); whilst in transgenic Brassica napus with inhibit-expressed SEQ ID NO: 1 (Zn-DN), SEQ ID NO: 1 gene expression was decreased to only half of that in control plant (Brassica napus, WT), see FIG. 6.

EXAMPLE 5

Identification of Heat Tolerance of Transgenic Plants Comprising SEQ ID NO: 1

Figure 4:
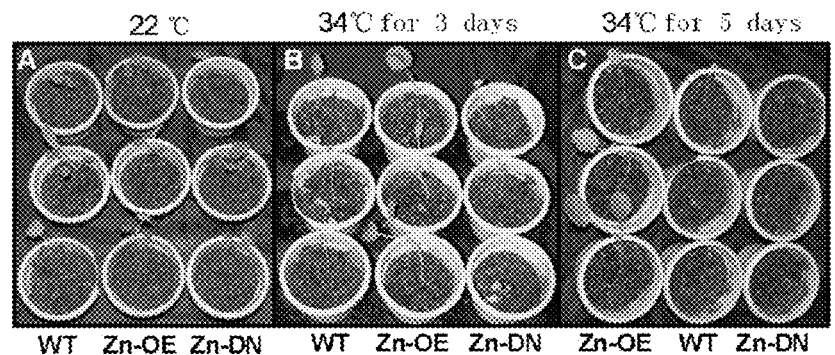
FIG. 4 shows photos comparing heat tolerance among transgenic *Brassica napus* lines with over- and inhibit-expressed SEQ ID NO: 1 and non-transgenic *Brassica napus*.

Seeds of transgenic Brassica napus lines comprising over- and inhibit-expressed SEQ ID NO: 1 from example 4 were respectively placed on moist filter papers for germination. After shell breaking, they were transferred into humus soil and cultured at 22° for about 15 days (with the growth of two pieces of euphylla), then transferred into heat stress of 34° under conditions of 14 h in sunlight and 10 h in dark. After being treated with heat stress for 3 days, growth of non-transgenic Brassica napus was inhibited, the transgenic Brassica napus line comprising inhibit-expressed SEQ ID NO: 1 began to die, and the transgenic Brassica napus plant comprising over-expressed SEQ ID NO: 1 grew normally (see FIG. 4-B and FIG. 5-A). After being treated with heat stress for 5 days, both non-transgenic Brassica napus and the transgenic Brassica napus line comprising inhibit-expressed SEQ ID NO: 1 had died, while the transgenic Brassica napus plant comprising over-expressed SEQ ID NO: 1 survived and grew normally (see FIG. 4-C and FIG. 5-B).

Results showed that, the heat tolerance of transgenic Brassica napus plant comprising over-expressed SEQ ID NO: 1 was enhanced, while that of transgenic Brassica napus plant comprising inhibit-expressed SEQ ID NO: 1 was reduced, illustrating that the expression product of SEQ ID NO: 1 was related to heat tolerance property.

EXAMPLE 6

Expression and Detection of the Polypeptide of SEQ ID NO: 2

1. Construction of Recombinant Plasmid Containing Target Gene

Primers were designed according to the nucleotide sequence of SEQ ID NO: 1, with

```
upstream primer (SEQ ID NO: 19):
5'-CCGGAATTCATGTCGGATCATTTGAGTTTATG-3',
and downstream primer (SEQ ID NO: 20):
5'-GCTCTAGATC AGACTGGTGTTGGGTTGGATAT-3'.
```

The nucleotide sequence of SEQ ID NO: 1 was amplified by PCR from Brassica napus cDNA.

PCR procedure was as follows:

| | |
|---|---|
| 1. 95° | 4 min (pre-denaturatior |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (see publications of Qiagen corp.), then digested with EcoR1 and Xbal1, recovered from gel and ligated into procaryotic expression vector pGEX-2T (ligation sites: EcoR1 and Xbal1), to obtain recombinant plasmid comprising SEQ ID NO: 1 gene, which was then transformed into *E. coli* strain BL21.

2. Induction and Purification of Target Protein Expression (1) One colony was picked up respectively from the control bacteria (BL21+pGEX-2T, defined as GTK) and that comprising recombinant plasmid (BL21+pGEX-2T-SEQ ID NO: 1, defined as GTK-Zn), and then inoculated into LB medium containing ampicillin (50 ug/ml) and cultivated overnight at 37°.

(2) 5 ml of the culture was inoculated into LB medium containing ampicillin (50 ug/ml) and incubated at 37° in a shaking incubator until $OD_{600}$=0.6-0.8. Then isopropyl β-D-1-thiogalactopyranoside (IPTG) was added to a final concentration of 1 mmol/L and the incubation was continued at 30° for 4 h.

(3) Cells were harvested by centrifugation at 5000 g for 10 min.

(4) Cell precipitation from every 100 ml of the culture was resuspended in 4 ml of PBS.

(5) Cells were lysed by sonication until the suspension was clear.

(6) The content was centrifuged with 10000 g at 4° for 30 min and the supernatant was transferred into a new tube.

(7) Cell lysates were homogenated with 50% glutathione-agarose resin, wherein 2 ml of resin was added into every 100 ml of cell culture; and the solution was shaken gently for 30 min at room temperature.

(8) The content was centrifuged with 500 g at 4° for 5 min and the supernatant was decanted.

(9) PBS of 10-folds of the bed volume was added into the precipitate and mixed by inverting the tube several times to rinse un-conjugated proteins.

(10) The content was centrifuged with 500 g at 4° for 5 min and the supernatant was decanted.

(11) The conjugated GST fusion protein was eluted with elution buffer.

(12) Results were analyzed with SDS polyacrylamide gel electrophoresis.

The results showed that, in *E. coli*, the induced expression of pGEX-2T (GTK-Zn) recombinant plasmid comprising the gene of SEQ ID NO: 1 resulted in identical protein band as anticipated (58 KD), see FIG. 7.

EXAMPLE 7

Substitution and Deletion in SEQ ID NO: 1, the Expression in *E. coli* and Heat Tolerance Analysis Thereof 1. Substitution and Deletion in the Nucleotide Sequence of SEQ ID NO: 1

Primers were designed according to the nucleotide sequence of SEQ ID NO: 1, with

```
upstream primer (SEQ ID NO: 21):
5'-ATGGCTGATGATTTCAGTTTATGTAC-3';
and downstream primer (SEQ ID NO: 22):
5'-TTGGGTTGGATATTGGCGGCGGCTG-3'.
```

PCR amplification was performed with vector pET28 ligated with SEQ ID NO: 1 as a template to obtain the sequence of SEQ ID NO: 5 (Ser at $2^{nd}$ position of the N-terminal of the sequence of SEQ ID NO: 2 being substituted with Ala, and Leu at $5^{th}$ position with Phe, with 3 amino acids deletion at C-terminal; which encodes the amino acid sequence of SEQ ID NO: 6), which was then ligated into pGEM-T vector.

2. Construction of Recombinant Plasmid Comprising the Nucleotide Sequence of SEQ ID NO: 5 and Molecular Verification Primers were designed to amplify the whole sequence encoding SEQ ID NO: 5, with

```
upstream primer (SEQ ID NO: 23):
5'-CCGGAATTCATGGCTGATGATTTCAG TTTATGTAC-3',
and downstream primer (SEQ ID NO: 24):
5'-CCGGAGCTCTTGGGTTGGATATTGGCGGCGGCTG-3'
```

The nucleotide sequence of SEQ ID NO: 5 was amplified by PCR from pGEM-T vector ligated with SEQ ID NO: 5.

PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (see publications of Qiagen corp.), then digested with BamH1 and Sac1, recovered from gel and ligated into pET28 (ligation sites: BamH1 and Sac1), to obtain the recombinant plasmid comprising SEQ ID NO: 5. Then *E. coli* was transformed with the recombinant plasmid comprising SEQ ID NO: 5 and plated onto LB agar containing Amp. The *E. coli* pET28 strain containing recombinant plasmid of SEQ ID NO: 4 was obtained after sequencing.

3. Verification of the Heat Tolerance of *E. coli* pET28 Strain Containing Recombinant Plasmid of SEQ ID NO: 5

Figure 8:
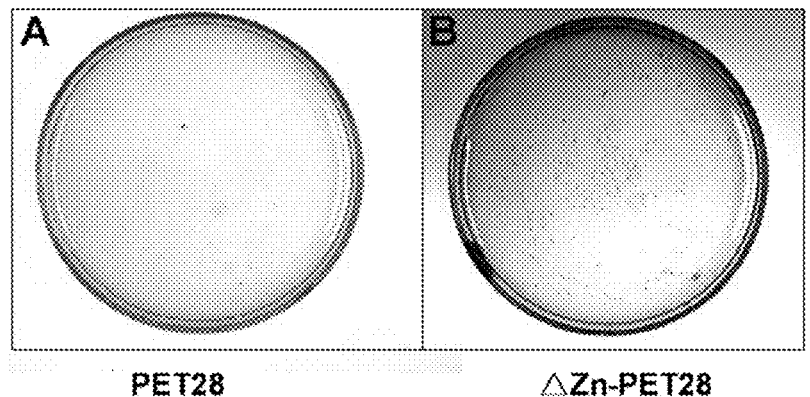
FIG. 8 shows growth status photos of *E. coli* containing recombinant plasmid comprising nucleotide sequence derived from substitution and deletion of SEQ ID NO: 1 (sequence of SEQ ID NO: 4) and *E. coli* containing pET28 at 42°, illustrating that nucleotide sequence derived from substitution and deletion of SEQ ID NO: 1 can also enhance the heat tolerance of bacteria.

*E. coli* pET28 strain containing recombinant plasmid of SEQ ID NO: 5 and the control of *E. coli* pET28 host strain were plated onto LB agar containing isopropyl β-D-1-thiogalactopyranoside (IPTG) at the same inoculation amount ($OD_{600}$=0.3), respectively, and cultured overnight at 42°. The control of *E. coli* pET28 host strain could not grow after being treated at 42° (see FIG. 8-A); while *E. coli* pET28 strain containing recombinant plasmid of SEQ ID NO: 5 grew well at 42° (see FIG. 8-B).

The results showed that the expression of substituted and deleted nucleotide sequence of SEQ ID NO: 1, such as the nucleotide sequence of SEQ ID NO: 5, possessed the same function of heat tolerance in *E. coli*.

EXAMPLE 8

Effects of Drought Stress to Seed Germination and Seedling Survival of Transgenic *Brassica napus*

Usually, PEG, mannitol and sucrose may be used in the lab to simulate drought conditions to detect growth status of plants. Researches of Hohl et al. on the above-mentioned stress agents supported the use of PEGs as osmosis reagent to study water relationship of plants. PEG with molecular weight of 6000 performs better than those with lower molecular weights, such as PEG1000 or 2000, probably because PEG6000 cannot get into plant cells to cause damage with its higher molecular weight. The sucrose solution, which usually causes the growth of moulds, generally is not used as osmosis reagent. Therefore, PEG 6000 was used in the present example to simulate drought stress conditions.

100 of uniform, plump and healthy seeds from 3 lines of above-mentioned transgenic type of *Brassica napus* (OE) as well as non-transgenic wild type (WT) were germinated. 8 layers of absorbent paper were introduced into a plate, with one layer of filter paper further added as germination bed. The germination bed of the treatment group was added with 10% of PEG6000 solution. For the control group, 100 of uniform, plump and healthy seeds from 3 lines of transgenic type (OE) as well as non-transgenic wild type (WT) were germinated, wherein 10 mL of distilled water was added. Germination was carried out at a constant temperature of 25° indoors under natural sunlight. The amount of seedlings survived was detected in 7 days to calculate the seedling rate. 10 seedlings were selected randomly to detect the seedling height, taproot length as well as fresh weight of single plant. The experiments were repeated for 3 times, with methods of calculation and determination as follows:

Relative germination rate=(treatment germination rate/control germination rate)×100%;

Relative seedling height=(treatment seedling height/control seedling height)×100%;

Relative fresh weight=(treatment fresh weight/control fresh weight)×100%;

Relative vitality index=(treatment seedling rate×treatment seedling height)/(control seedling rate×control seedling height)×100%;

Results showed that (see Table 2) the seed germination rate and the seedling growth status of TT1-transgenic *Brassica napus* were better than those of wild type.

TABLE 2

Effects of drought stress on seed germination and seedling survival of TT1-transgenic *Brassica napus*

| | Relative germination rate (%) | Relative seedling height (%) | Relative fresh weight (%) | Relative vitality index (%) |
|---|---|---|---|---|
| OE (1) | 91.4 | 69.8 | 69.1 | 63.8 |
| OE (2) | 90.6 | 70.9 | 68.6 | 64.2 |
| OE (3) | 92.2 | 76.1 | 70.4 | 70.2 |
| WT | 58.5 | 59.4 | 68.6 | 34.8 |

EXAMPLE 9

Effects of Drought Stress on Proline (Pro) Content of Transgenic *Brassica napus*

1. Standard Curve Drawing (1) 25 mg of proline was precisely weighed with analytical balance and introduced into a beaker to be dissolved with small amount of distilled water, then transferred into a 250 ml volumetric flask, and distilled water was added to the scale, wherein 100 μg of proline was contained in every milliliter of the standard solution.

(2) 2 ml of proline solution of a series of the standard concentrations, 2 ml of acetic acid and 2 ml of acidic ninhydrin solution was added into 6 tubes, respectively, and heated in boiling water bath for 30 min.

(3) After cooled, 4 ml of toluene was precisely added into every tube, followed by oscillating for 30 s and letting stand for a moment to transfer all the pigment into toluene solution.

(4) The proline toluene solution was gently transferred with injectors from every upper tube into cuvettes, to perform colorimetry at 520 nm with toluene solution as a blank control.

(5) Standard curve drawing: first, the regression equation of absorbance (Y) vs. proline concentration (X) was calculated, followed by drawing a standard curve according to the regression equation to calculate the proline content in 2 ml of solution assayed (μg/2 ml).

2. Sample Assays (1) Proline extraction: 0.2-0.5 g of leaves was precisely weighed from *Brassica napus* (3 lines of transgenic brassica prepared as above and the wild type, 3 plants for each) cultivated under the same routine conditions for 30 days and introduced into tubes. Then 5 ml of 3% sulphosalicylic acid solution was added in each tube and extraction was performed in boiling water bath for 10 min (with constant shakings during extraction). After cooled, the solution was filtered into clean tubes, with the filtrate as proline extract.

(2) 2 ml of proline extract, 2 ml of acetic acid and 2 ml of acidic ninhydrin solution were added into another clean tube with a glass plug and heated in boiling water bath for 30 min, wherein the solution became red.

(3) After cooled, 4 ml of toluene was added into the tube, followed by oscillating for 30 s, letting stand for a moment, taking the upper solution into a 10 ml centrifugation tube and centrifuging at 3000 rpm for 5 min.

(4) The upper red proline toluene solution was transferred gently with a suction tube into a cuvette to perform colorimetry at 520 nm with toluene solution as blank control to obtain the absorbance.

3. Results Calculation

Figure 9:
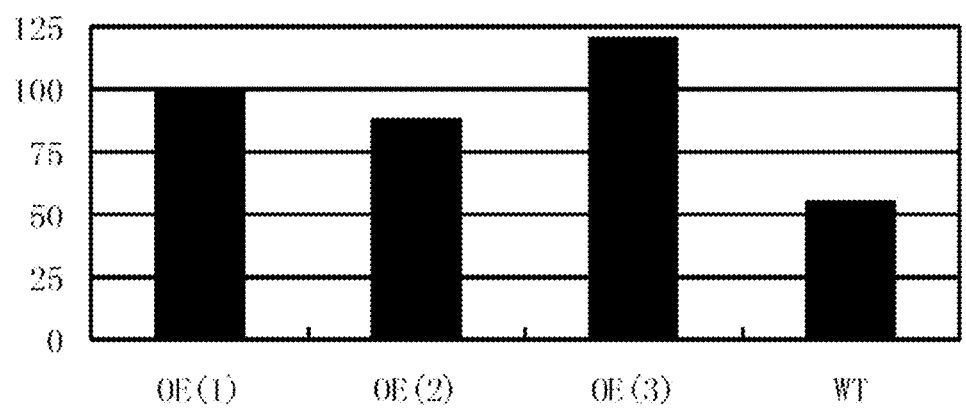
FIG. 9 shows the result of proline (Pro) content detected from TT1-transgenic *Brassica napus* after drought stress, wherein OE (1), OE (2) and OE (3) are 3 transgenic *Brassica napus* lines with over-expressed TT1 gene; WT is wild type *Brassica napus*; and the ordinate means proline content as μg/g.

The proline content (X μg/2 ml) of the 2 ml assayed solution was found out from standard curve, followed by calculating the proline content percentage in the sample with the equation of: proline content (μg/g)[X×5/2]/sample weight (g), and obtaining the average value, see FIG. 9.

It was found with the calculation that the proline content of SEQ ID NO: 1 transgenic *brassica* OE (1), OE (2) and OE (3) was indeed larger than that of the wild type, wherein the content of OE (3) was extremely high. With major activities of osmoregulation reagent, reductant or energy source, reserve material for N element, free radical scavenger of hydroxy, protectant for enzymes in cells, decreasing the acidity of cells and regulating redox potential, proline played an important role on the accommodation of plant cells to stresses. Therefore, tolerance of TT1-transgenic *Brassica napus* to osmosis stress from drought was better than that of the wild type under normal culture conditions.

EXAMPLE 10

Test for Drought Tolerance of SEQ ID NO: 1 Transgenic *Brassica napus* Plants at Seedling Stage

Figure 10:
FIG. 10 shows photos at the day of ceasing watering, with left as wild type and right as transgenic type.
Figure 11:
FIG. 11 shows photos after 5 days of ceasing watering, with left as wild type and right as transgenic type.

*Brassica napus* seedlings (both wild and transgenic type) cultured at normal conditions for 20 days were treated with drought by ceasing watering for 8 days, and the growth status was observed regularly. Results were as followings: no difference appeared at the day of ceasing watering (see FIG. 10); after 5 days of ceasing watering, the growth of wild type seedlings had stopped and all leaves were withered (see FIG.

Figure 12:
FIG. 12 shows photos after 8 days of ceasing watering, with left as wild type and right as transgenic type.

11), while those of TT1-transgenic type could still grow and keep 1-2 green leaves; and after 8 days of ceasing watering, wild type seedlings thoroughly died from drought, while those of TT1-transgenic type survived and even kept 1-2 fresh green leaves (see FIG. 12).

EXAMPLE 11

Preparation of SEQ ID NO: 1 Transgenic *Arabidopsis thaliana* Plant and Obtaining the Seed Thereof 1. Obtaining Transgenic *Arabidopsis thaliana* Plant and Seeds Thereof Primers were designed according to the nucleotide sequence of SEQ ID NO: 1, with

```
upstream primer (SEQ ID NO: 25):
5'-CGCGGATCCATGTCGGATCATTTGAGTTTATG-3',
and downstream primer (SEQ ID NO: 26):
5'-CCGGAGCTCTCAGACTGGTGTTGGGTTGGATAT-3'.
```

The whole nucleotide sequence of SEQ ID NO: 1 was amplified by PCR from *Brassica napus* cDNA.

PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. Steps 2-4 | cycle for 30 times |
| 6. 72° | 5 min (final elongation) |
| 7. Conservation at 4°. | |

The PCR product was purified (see the manual of PCR product purification kit of Qiagen corp.), then digested with BamH1 and Sac1, recovered from gel and ligated into vector pBI121 (ligation sites: BamH1 and Sac1), to obtain recombinant plasmid comprising over-expressed SEQ ID NO: 1, which was transformed into *Agrobaterium*. *Arabidopsis thaliana* was then transformed by inflorescence infection with detailed steps as follows:

A. *Agrobaterium* containing recombinant plasmid comprising over-expressed SEQ ID NO: 1 was inoculated into LB medium containing 20 mg/L of Str, 50 mg/L of Kan and 40 mg/L of Rif, and cultivated overnight at 28°. Cells were collected and resuspended with MS medium containing 0.01% of the surfactant silwet-77 till $OD_{600}$=0.4-0.6, followed by incubating at 28° for 1-2 h and keeping the bacteria liquid.

B. The inflorescence of *Arabidopsis thaliana* cultured for 60 days was cut off and immersed with the bacteria liquid of *Agrobaterium* containing recombinant plasmid comprising over-expressed SEQ ID NO: 1 for 2 min. After cultivating in dark for 48 hours, the result *Arabidopsis thaliana* seedlings was transferred in a normal illumination environment, with resulted legumes as the T0 generation of TT1-transgenic seeds.

2. Transgenic Identification

The resulted seeds were planted and after 50 days of growth, a few leaves were picked up for PCR detection, with

```
upstream primer (SEQ ID NO: 27):
5' ATTTCATTTGGAGAGAACACGG 3',
and downstream primer (SEQ ID NO: 28):
5' TCAGACTGGTGTTGGGTTGGATAT 3'.
```

Primers were designed according to the nucleotide sequence of SEQ ID NO: 1,

PCR procedure was as follows:

| | |
|---|---|
| 1. 95° | 4 min (pre-denaturation) |
| 2. 95° | 30 s (denaturation) |
| 3. 53° | 30 s (annealing) |
| 4. 72° | 50 s (elongation) |
| 5. 2-4 step | cycle for 37 times |
| 6. 72° | 5 min (final elongation) |
| 7. Conservation at 4°. | |

Figure 13:
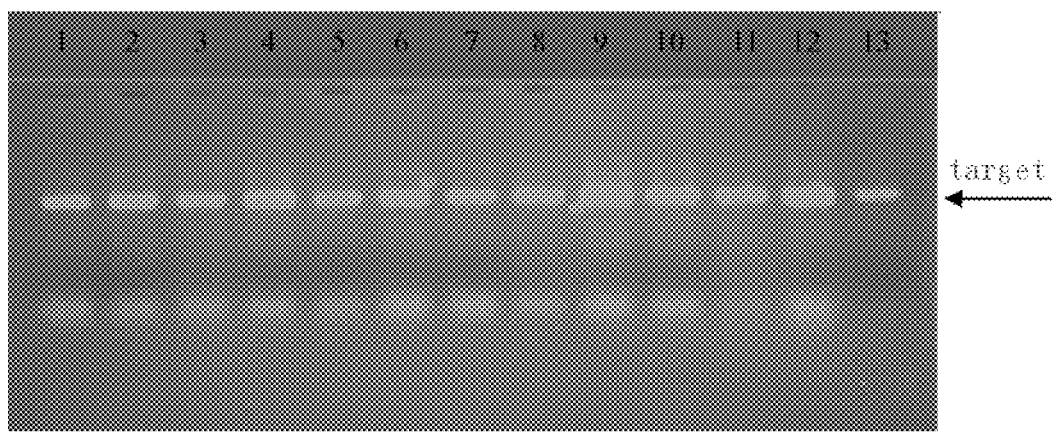
FIG. 13 shows a photo of detecting with agarose electrophoresis whether target gene is transformed into *Arabidopsis thaliana*, wherein lines 1-12 are transgenic *Arabidopsis thaliana* genomic DNA, and line 13 is over-expressed recombinant plasmid DNA comprising SEQ ID NO: 1.

Then agarose electrophoresis was performed to detect the presence of target band, which was an indication that the target gene had been transformed into *Arabidopsis thaliana*, see FIG. 13.

As shown in FIG. 13, lines 1-12 were transgenic *Arabidopsis thaliana* genomic DNA, and line 13 was the over-expressed recombinant plasmid DNA comprising SEQ ID NO: 1. The target band of the DNA detected was identical with those of over-expressed plasmid DNA, indicating that it was the positive transgenic plant comprising over-expressed nucleotide of SEQ ID NO: 1; and the seed thereof was prepared.

3. After the maturation of positive transgenic plants, seeds were collected for reservation. Similarly, *Arabidopsis thaliana* plants comprising over-expressed SEQ ID NO: 3 and seeds thereof were prepared.

EXAMPLE 12

Effects of Various NaCl Concentrations on the Germination Rate of *Arabidopsis thaliana* Seeds Saline-alkaline soil usually contains salts of NaCl, $Na_2SO_4$, $Na_2CO_3$ and $NaHCO_3$. Besides decreasing the water potential, saline stress also includes the ionic stress from the increased sodium ion, which affects the absorbance of plants to nutrients like potassium ion and calcium ion, thus causing damages to plants. Therefore, NaCl was utilized to simulate the saline stress condition in the present experiment.

NaCl was added before sterilization into MS culture medium (see Table 3, with pH adjusted to 5.8 with KOH) to the final concentration of 0 mmol/L (control), 50 mmol/L, 100 mmol/L, 150 mmol/L, 200 mmol/L, 250 mmol/L and 300 mmol/L. The culture medium was separately loaded into plates after being sterilized with high-pressure steam. After solidified, the culture medium was inoculated with 2 ml of seeds suspended in sterile water, the spare of which was removed after seeding well. The plate cover was opened to dry the medium surface at sterile environment for 1 h. The plate was sealed and cultivated in a culture chamber (22°; intensity of illumination, 6000-8000 1×; light-dark cycle, 16 h/8 h; and relative humidity, 70%) with 3 repetitions for each treatment. Germination and other phenotypes were observed every day for the statistics of germination number and the average was calculated.

TABLE 3

Components of MS culture medium

| | Components | Conc. (mg/L) |
|---|---|---|
| Major elements | Potassium nitrate ($KNO_3$) | 1900 |
| | Ammonium nitrate ($NH_4NO_3$) | 1650 |
| | Potassium dihydrogen phosphate ($KH_2PO_4$) | 170 |
| | Magnesium sulfate ($MgSO_4 \cdot 7H_2O$) | 370 |
| | Calcium chloride ($CaCl_2 \cdot 2H_2O$) | 440 |
| Minor elements | Potassium iodide (KI) | 0.83 |
| | Boric acid ($H_3BO_3$) | 6.2 |
| | Manganese sulfate ($MnSO_4 \cdot 4H_2O$) | 22.3 |
| | Zinc sulfate ($ZnSO_4 \cdot 7H_2O$) | 8.6 |
| | Sodium molybdate ($Na_2MoO_4 \cdot 2H_2O$) | 0.25 |
| | Copper sulfate ($CuSO_4 \cdot 5H_2O$) | 0.025 |
| | Cobalt chloride ($CoCl_2 \cdot 6H_2O$) | 0.025 |
| Ferric salts | Disodium ethylenediamine tetraacetic acid ($Na_2 \cdot EDTA$) | 37.3 |
| | Ferrous sulfate ($FeSO_4 \cdot 7H_2O$) | 27.8 |
| Organic components | Inositol | 100 |
| | Glycine | 2 |
| | Thiamine hydrochloride (VB1) | 0.1 |
| | Pyridoxine hydrochloride (VB6) | 0.5 |
| | Nicotinic acid (VB5 or VPP) | 0.5 |
| | Sucrose | 30 g/L |
| | Agar | 7 g/L |

Figure 14:
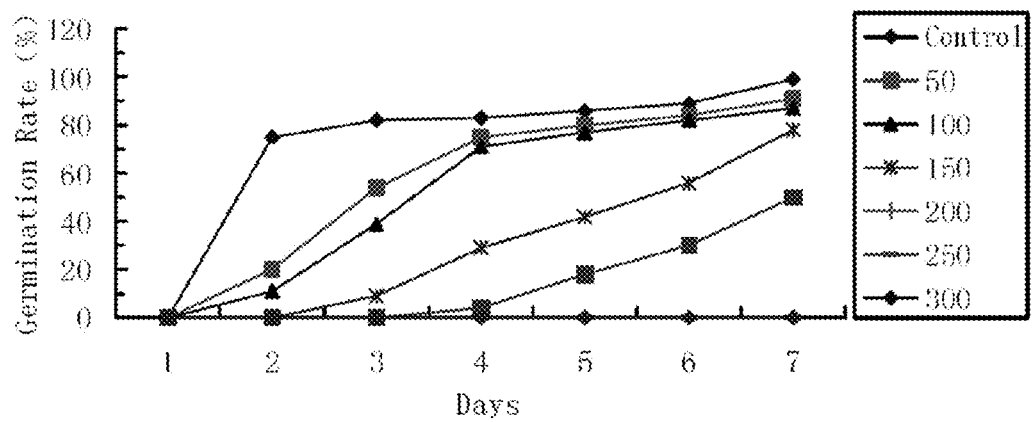
FIG. 14 shows a diagram illustrating effects of NaCl of various concentrations (mmol/L) on germination rate of non-TT1-transgenic *Arabidopsis thaliana* seeds.
Figure 15:
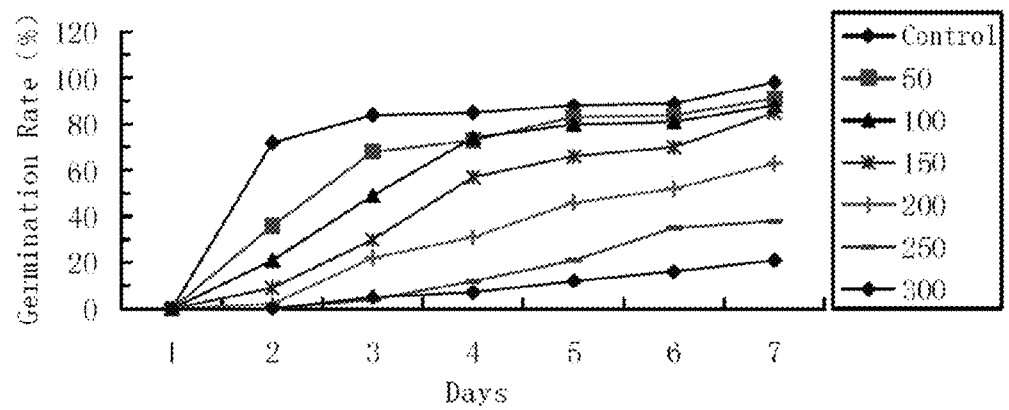
FIG. 15 shows a diagram illustrating effects of NaCl of various concentrations (mmol/L) on germination rate of *Arabidopsis thaliana* seeds with over-expressed TT1 gene.

Results showed that non-transgenic *Arabidopsis thaliana* seeds appeared sensitive to the variation of NaCl concentrations (see FIG. 14) and even seldomly sprouted at 250 mM and 300 mM; while TT1-transgenic *Arabidopsis thaliana* seeds showed better tolerance to NaCl (see FIG. 15) with relatively high final germination rate of seeds at 50 mM, 100 mM and 150 mM of concentrations and kept certain germination rate even at 200 mM, 250 mM and 300 mM of concentrations, and the germination rates thereof were significantly higher than that of non-transgenic type.

EXAMPLE 13

Effects of Various NaCl Concentrations on the Proline (Pro) Content of *Arabidopsis thaliana*

1. Standard Curve Drawing with Chromogenic Ninhydrin Solution (1) 25 mg of proline with analytical balance was weighed precisely and introduced into a beaker to be dissolved with a small amount of distilled water, then transferred into a 250 ml volumetric flask and distilled water was added to the scale, wherein 100 μg of proline was contained in every milliliter of the standard solution.

(2) 2 ml of proline solution of a series of standard concentration, 2 ml of acetic acid and 2 ml of acidic ninhydrin solution were added into 6 tubes, respectively, and heated in boiling water bath for 30 min.

(3) After cooled, 4 ml of toluene was precisely added into every tube, followed by oscillating for 30 s and letting stand for a moment to transfer all the pigment into toluene solution.

(4) The proline toluene solution was gently transferred with injectors from every upper tube into cuvettes, to perform colorimetry at 520 nm with toluene solution as blank control. (TU-1800 type ultraviolet spectrophotometer, Puxitong instrument corp., Beijing, China)

(5) Standard curve drawing: first the regression equation of absorbance (Y) vs. proline concentration (X) was calculated, followed by drawing a standard curve according to the regression equation to calculate the proline content in 2 ml of assayed solution (μg/2 ml).

2. Sample Assays (1) Proline extraction: 0.2-0.5 g of *Arabidopsis thaliana* seedlings (4 lines of transgenic and the wild type) was precisely weighed and introduced into tubes, and cultivated under the same condition for 20 days, respectively. 5 ml of 3% sulphosalicylic acid solution was added in each tube and extraction was performed in boiling water bath for 10 min (with constant shakings during extraction). After cooled, the solution was filtered into clean tubes, with the filtrate as proline extract.

(2) 2 ml of proline extract, 2 ml of acetic acid and 2 ml of acidic ninhydrin solution were added into another clean tube with a glass plug and heated in boiling water bath for 30 min, wherein the solution became red.

(3) After cooled, 4 ml of toluene was added into the tube, followed by oscillating for 30 s, letting stand for a moment, taking the upper solution into a 10 ml centrifugation tube and centrifuging at 3000 rpm for 5 min.

(4) The upper red proline toluene solution was gently transferred with a suction tube into a cuvette to perform colorimetry at 520 nm with toluene solution as blank control to obtain the absorbance.

3. Results Calculation

Figure 16:
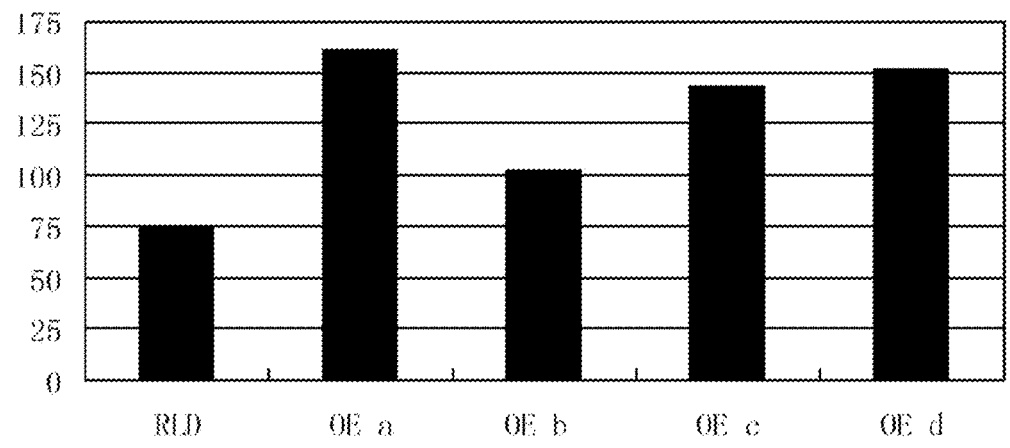
FIG. 16 shows a diagram illustrating proline contents (m/g) in different treatment groups, wherein RLD is the wild type; OEa, OEb, OEc and OEd are *Arabidopsis thaliana* lines comprising over-expressed TT1 gene; and the ordinate means proline content (μ/g).

The proline content (μg/2 ml) of the 2 ml assayed solution was found out from standard curve, then the proline content percentage in the sample was calculated with the equation of: proline content (μg/g)[X×5/2]/sample weight (g), and the average value was obtained, see FIG. 16.

Figure 17:
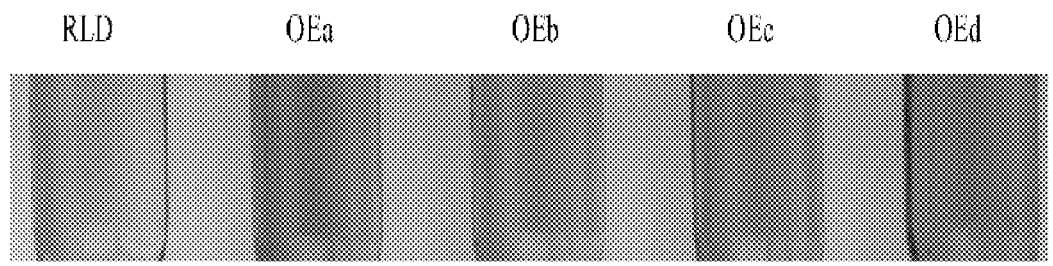
FIG. 17 shows images of red proline-toluene solution from different treatment groups in cuvettes, wherein RLD is the wild type; and OEa, OEb, OEc and OEd are *Arabidopsis thaliana* lines with over-expressed TT1 gene.

The experiment results of FIG. 17 showed that after being colored with ninhydrin, the color of RLD was light than those of OEa, OEb, OEc and OEd, wherein OEa and OEd showed obviously deeper color than others, illustrating that the proline expression of over-expressed lines was higher than that of the wild type RLD.

The calculation results showed that the proline content of TT1-transgenic *Arabidopsis thaliana* was higher indeed than that of the wild type RLD, wherein the content of OEa and OEd was extremely high (see FIG. 16).

With major activities of osmoregulation reagent, reductant or energy source, reserve material for N element, free radical scavenger of hydroxy, protectant for enzymes in cells, decreasing the acidity of cells and regulating redox potential, proline played an important role on the accommodation of plant cells to stresses. Therefore, tolerance of TT1-transgenic *Arabidopsis thaliana* to the osmosis stress from saline-alkaline was better than that of the wild type under normal culture conditions.

EXAMPLE 14

Growth Experiments of Transgenic Microbes Comprising SEQ ID NO: 1 Gene in Various pHs Preparation of culture medium: LB culture medium was prepared with the addition of antibiotics of Kan 50 ug/ml and Cam 50 ug/ml as well as 0.1 mM of IPTG, and was split charged to adjust pHs of 4.0, 5.5, 7.0, 8.5 and 10.0 in different tubes, with 2 tubes at one pH and 5 ml in each tube.

Preparation of bacteria suspension: Single colonies of TT1-transgenic *E. coli* pET28 and non-transgenic *E. coli* were activated overnight at 37°.

Dropwise addition of sample bacteria: 0.05 ml of activated bacteria liquid was added into tubes containing LB culture medium of various pHs, followed by shaking and cultivating (37°, 225 rpm, 14 h).

Figure 18:
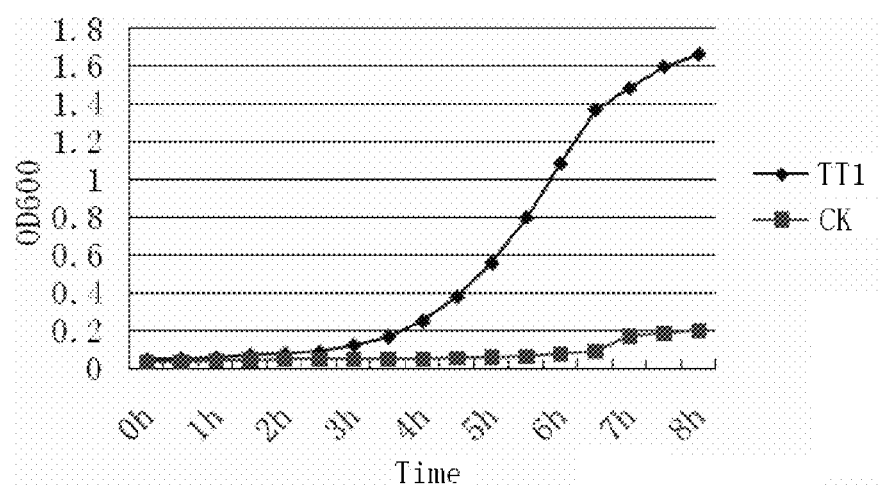
FIG. 18 shows a diagram illustrating growth status of TT1-transgenic and non-transgenic *E. coli* at pH4.0 and 37°. The ordinate means OD600 values, and the abscissa the culture time.
Figure 19:
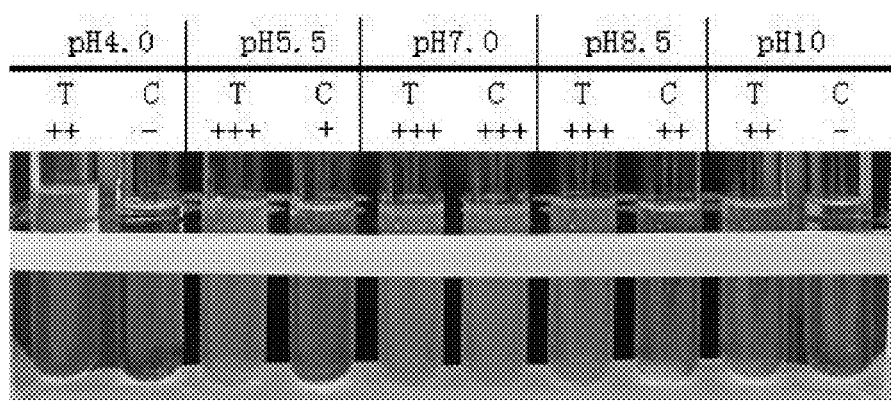
FIG. 19 shows photos of growth status of TT1-transgenic *E. coli* (T) and non-transgenic *E. coli* (C) at 37° for 14 h, with pH values of 4.0, 5.5, 7.0, 8.5 and 10.0, respectively.

Culture and observation: The growth status of TT1-transgenic *E. coli* was observed with naked eyes at 37° for 14 h in various pHs ("−" stands for non-growth, "+" for slight growth, "++" for well growth and "+++" for bacteria liquid of high concentration), see FIG. 19; meanwhile, OD values were detected at regular times to draw growth curves of different pHs, see FIG. 18.

Results showed that transgenic *E. coli* comprising the heat tolerant gene TT1 possessed with higher saline-alkaline tolerance than that of non-transgenic. At the normal pH condition (pH7.0), the growth status of the TT1-transgenic (T) and the non-transgenic (C) was substantially the same with basically identical bacteria liquid concentrations, as shown in figures. However, at acidic conditions, the growth status of the two was different: as shown in figures, at pH5.5, the TT1-transgenic (T) showed higher bacteria liquid concentration, while the non-transgenic lower; and at pH4.0, the TT1-transgenic (T) showed higher bacteria liquid concentration, while non-transgenic bacteria barely grew. With alkaline conditions, the growth status of the TT1-transgenic (T) and the non-transgenic (C) was also different: as shown in figures, at pH8.5, the TT1-transgenic (T) showed higher bacteria liquid concentration, while the non-transgenic lower; and at pH10, the TT1-transgenic (T) showed higher bacteria liquid concentration, while non-transgenic bacteria barely grew.

The growth status of TT1-transgenic and non-transgenic *E. coli* was detected at regular times at 37° and pH4.0 (TU-1800 type ultraviolet spectrophotometer, Puxitong instrument corp., Beijing, China). Larger OD values meant larger bacteria liquid concentrations. As shown in figures, the gradient of the growth curve of TT1-transgenic *E. coli* was obviously larger than that of the non-transgenic as time changed, illustrating obviously faster growth rate of the TT1-transgenic *E. coli* than that of the non-transgenic.

EXAMPLE 15

Preliminary Studies on Mechanisms for the Enhancement of SEQ ID NO: 1 Gene on the Tolerance to Abiotic Stresses In the present invention, genomic expression of *E. coli* comprising over-expressed TT1 gene was compared with that of blank control *E. coli* by using gene chips of "*E. coli* CHIP Version 2.0" from TaKaRa (Dalian, China) corp. ltd.

according to the manual (with standard for gene selection shown in Table 4), for the preliminary study of the mechanism for the enhancement of TT1 gene on the acidic-alkaline tolerance of microbes as well as the saline-alkaline tolerance of plants.

Control group: *E. coli* (Cy3) transformed with empty pET28a; Experimental group: *E. coli* (Cy5) transformed with TT1-pET28a.

TABLE 4

Standard for gene selection

| Cy5/Cy3_ratio (G) | Cy5/Cy3_ratio (G) | Cy3_S-B (G) | Cy5_S-B (G) | Cy3_posi | Cy5_posi |
|---|---|---|---|---|---|
| >=2 | | >=200 | | 1 | |
| >=2 | | >=200 | | | 1 |
| >=2 | | | >=200 | 1 | |
| >=2 | | | >=200 | | 1 |
| | <=0.5 | >=200 | | 1 | |
| | <=0.5 | >=200 | | | 1 |
| | <=0.5 | | >=200 | 1 | |
| | <=0.5 | | >=200 | | 1 |

Analysis of gene chip detection: The total genome of *E coli*. possesses with about 4400 of different encoded genes. Analysis with gene chips was performed in the present invention for studies of genes interacted with TT1 gene in *E. coli*. Results showed that genes of yabF, rhsE, yhcP, yzpK and yhiR were expressed with up-regulation because of TT1, wherein yabF, rhsE and yhcP of such up regulated expressed genes were found to relate with ion channels by further studies. Therefore, it is possible that TT1 balances the osmosis of ions in and out of cells by interacting with proteins relating to regulations of certain ion channels, thus decreasing damages from excessive ions. The above-mentioned results had provided research foundations for the mechanism of the acidic-alkaline tolerance of microbes as well as the saline-alkaline tolerance of plants.

The invention claimed is:

1. An isolated or synthetic polynucleotide comprising the nucleotide sequence of SEQ ID NO: 1 or derivatives thereof in which one nucleotide is added to, deleted from, or substituted into SEQ ID NO: 1, wherein said polynucleotide encodes a polypeptide that enhances the tolerance of plants or microbes to at least one stress selected from the group consisting of drought, acid-alkaline, saline-alkaline, and heat stress.

2. The polynucleotide according to claim 1, wherein the polynucleotide comprises the nucleotide sequence of SEQ ID NO: 1.

3. A polynucleotide comprising the nucleotide sequence of SEQ ID NO: 5.

4. An isolated or synthetic polypeptide comprising:
   (1) the amino acid sequence of SEQ ID NO: 2 or SEQ ID NO: 6; or
   (2) a derivative of SEQ ID NO: 2 or SEQ ID NO: 6 in which one amino acid is added to, deleted from, or substituted into SEQ ID NO: 2 or SEQ ID NO: 6, wherein the overexpression of said polypeptide in a plant or microbe enhances the tolerance of the plant or microbe to at least one stress selected from the group consisting of drought, acid-alkaline, saline-alkaline, and heat stress.

5. A cDNA encoding said polypeptide of claim 4.

6. A method for enhancing a tolerance of plants or microbes to at least one stress, said method comprising:
   (a) transforming a plant cell or microbe with a construct comprising the polynucleotide of claim 1, wherein said polynucleotide is operably linked to a promoter; and
   (b) regenerating a transgenic plant or microbe from the plant cell or microbe of step (a), wherein the transgenic plant or microbe overexpresses said polynucleotide such that the transgenic plant or microbe exhibits enhanced tolerance to said at least one stress selected from the group consisting of drought, acid-alkaline, saline-alkaline, and heat stress.

7. A method for enhancing a tolerance of plants or microbes to at least one stress, said method comprising:
   (a) transforming a plant cell or microbe with a construct comprising a nucleotide sequence that encodes the polypeptide of claim 4, wherein said nucleotide sequence is operably linked to a promoter; and
   (b) regenerating a transgenic plant or microbe from the plant cell or microbe of step (a), wherein the transgenic plant or microbe overexpresses said polypeptide such that the transgenic plant or microbe exhibits enhanced tolerance to said at least one stress selected from the group consisting of drought, acid-alkaline, saline-alkaline, and heat stress.

8. A recombinant vector comprising said polynucleotide of claim 1.

9. The recombinant vector according to claim 8, wherein the recombinant vector expresses a protein encoded by said polynucleotide, wherein said polynucleotide is operably linked to a promoter.

10. The recombinant vector according to claim 9, wherein said recombinant vector is a recombinant plasmid.

11. A host cell containing said recombinant vector of claim 8.

12. A transgenic plant or microbe containing said recombinant vector of claim 8, wherein said polynucleotide is operably linked to a promoter.

13. A method of producing transgenic plants comprising the following steps:
   (1) creating a recombinant expression vector comprising the isolated or synthetic polynucleotide of claim 1 operably linked to a plant promoter, wherein said polynucleotide comprises SEQ ID NO: 1;
   (2) transforming plants cells with the recombinant expression vector of step (1); and
   (3) regenerating transgenic plants and progeny thereof from the transformed plant cells of step (2), wherein said progeny thereof includes seeds and plant tissues, wherein said seeds and plant tissues comprise the polynucleotide.

14. A method of producing transgenic microbes comprising the following steps:
   (1) creating a recombinant expression vector comprising the isolated or synthetic polynucleotide of claim 1 operably linked to a microbe promoter, wherein said polynucleotide comprises SEQ ID NO: 1;
   (2) transforming microbe cells with the recombinant expression vector of step (1); and
   (3) producing transgenic microbes from the transformed microbe cells of step (2).

* * * * *